United States Patent [19]
Feng et al.

[11] Patent Number: 5,998,362
[45] Date of Patent: Dec. 7, 1999

[54] CONJUGATES USEFUL IN THE TREATMENT OF PROSTATE CANCER

[75] Inventors: Dong-Mei Feng; Victor M. Garsky, both of Blue Bell; Raymond E. Jones, Lansdale; Jenny M. Wai, Harleysville, all of Pa.

[73] Assignee: Merck & Co., Inc., Rahway, N.J.

[21] Appl. No.: 08/926,412

[22] Filed: Sep. 9, 1997

Related U.S. Application Data

[60] Provisional application No. 60/026,015, Sep. 12, 1996.

[51] Int. Cl.$^6$ ............................. A61K 38/14; C07K 4/00
[52] U.S. Cl. ............................... 514/2; 514/12; 514/13; 514/14; 514/15; 514/16; 514/17; 514/18; 530/300; 530/322; 530/324; 530/325; 530/326; 530/327; 530/328; 530/329; 530/330; 424/185.1; 424/193.1; 424/194.1; 424/195.11
[58] Field of Search .......................... 424/193.1, 194.1, 424/195.11, 185.1; 514/12–18, 2, 8; 530/324–330, 322, 300

[56] References Cited

U.S. PATENT DOCUMENTS

| | | | |
|---|---|---|---|
| 4,296,105 | 10/1981 | Baurain et al. | 424/180 |
| 4,388,305 | 6/1983 | Trouet et al. | 424/177 |
| 4,703,107 | 10/1987 | Monsigny et al. | 530/330 |
| 4,870,162 | 9/1989 | Trouet et al. | 530/363 |
| 5,024,835 | 6/1991 | Rao et al. | 424/85.91 |
| 5,220,001 | 6/1993 | Ok et al. | 536/6.4 |
| 5,286,637 | 2/1994 | Veronese et al. | 435/183 |
| 5,464,820 | 11/1995 | Burton et al. | 514/16 |
| 5,599,686 | 2/1997 | DeFeo-Jones et al. | 435/23 |
| 5,693,751 | 12/1997 | Sakurai et al. | 530/322 |

FOREIGN PATENT DOCUMENTS

| | | |
|---|---|---|
| 2203622 | of 0000 | Canada . |
| 0 126 344 A2 | of 0000 | European Pat. Off. . |
| WO96/05863 | of 0000 | WIPO . |
| 9600503 | 1/1996 | WIPO . |

OTHER PUBLICATIONS

Science, vol. 261, pp. 212–215 (Jul. 9, 1993), by Trail, et al.

J. Med. Chem, vol. 29, No. 7, pp. 1273–1276 (1986), by Israel, et al.

J. Med. Chem., vol. 28, No. 8, pp. 1079–1088 (1985), by Rao, et al.

Proc. Natl. Acad. Sci. USA, vol. 83, pp. 3166–3170 (May 1986), by Watt, et al.

J. Med. Chem., vol. 34, pp. 3029–3035 (1991), by Mayer, et al.

Eur. J. Biochem, vol. 194, pp. 755–763 (1990), by Christensson, et al.

Anal. Biochem., vol. 193, pp. 248–255 (1991), by Harnois-Pontoni, et al.

Eur. J. Biochem., vol. 95, pp. 115–119 (1979), by Pazsgay, et al.

J. Med. Chem, vol. 26, No. 5, pp. 638–644 (1983), by Chakravarty, et al.

J. Med. Chem, vol. 26, pp. 633–638 (1983), by Chakravarty, et al.

*Primary Examiner*—Bennett Celsa
*Attorney, Agent, or Firm*—David A. Muthard; Mark R. Daniel

[57] ABSTRACT

Chemical conjugates which comprise oligopeptides, having amino acid sequences that are selectively proteolytically cleaved by free prostate specific antigen (PSA), hydrophilic oligopeptide blocking groups and known cytotoxic agents are disclosed. Such conjugates are useful in the treatment of prostatic cancer and benign prostatic hypertrophy (BPH).

10 Claims, No Drawings

SEQUENCE LISTING (1) GENERAL INFORMATION:

(iii) NUMBER OF SEQUENCES: 128

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Asn Lys Ile Ser Tyr Gln Ser
 1             5

(2) INFORMATION FOR SEQ ID NO:2:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Lys Ile Ser Tyr Gln Ser
 1          5

(2) INFORMATION FOR SEQ ID NO:3:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide

```
    (xi) SEQUENCE DESCRIPTION: SEQ ID NO:3:

Asn Lys Ile Ser Tyr Tyr Ser
1               5

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Asn Lys Ala Ser Tyr Gln Ser
1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Ser Tyr Gln Ser Ser
1               5

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

Lys Tyr Gln Ser Ser
1               5

(2) INFORMATION FOR SEQ ID NO:7:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine (xi) SEQUENCE DESCRIPTION: SEQ ID NO:7:

Xaa Tyr Gln Ser Ser
1               5

(2) INFORMATION FOR SEQ ID NO:8:

(i) SEQUENCE CHARACTERISTICS:
        (A) LENGTH: 5 amino acids
        (B) TYPE: amino acid
```

(C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: Homoarginine (xi) SEQUENCE DESCRIPTION: SEQ ID NO:8:

Xaa Cys Gln Ser Ser
 1               5

(2) INFORMATION FOR SEQ ID NO:9:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:9:

Tyr Gln Ser Ser
 1

(2) INFORMATION FOR SEQ ID NO:10:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:10:

Tyr Gln Ser Leu
 1

(2) INFORMATION FOR SEQ ID NO:11:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 4...4
            (D) OTHER INFORMATION: Norleucine (xi) SEQUENCE DESCRIPTION: SEQ ID NO:11:

Tyr Gln Ser Leu
 1

(2) INFORMATION FOR SEQ ID NO:12:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:

```
            (A) NAME/KEY: Other
            (B) LOCATION: 1...1
            (D) OTHER INFORMATION: Cyclohexylglycine (xi) SEQUENCE DESCRIPTION: SEQ ID NO:12:

Xaa Gln Ser Leu
 1

(2) INFORMATION FOR SEQ ID NO:13:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: Cyclohexylglycine
            (A) NAME/KEY: Other
            (B) LOCATION: 4...4
            (D) OTHER INFORMATION: Norleucine (xi) SEQUENCE DESCRIPTION: SEQ ID NO:13:

Xaa Gln Ser Leu
 1

(2) INFORMATION FOR SEQ ID NO:14:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

Asn Lys Ile Ser Tyr Gln Ser Ser
 1               5

(2) INFORMATION FOR SEQ ID NO:15:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Asn Lys Ile Ser Tyr Gln Ser Ala
 1               5

(2) INFORMATION FOR SEQ ID NO:16:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Ala Asn Lys Ile Ser Tyr Tyr Ser
 1               5
```

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Ala Asn Lys Ala Ser Tyr Gln Ser
 1               5

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Ser Tyr Gln Ser Ser Thr
 1               5

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Ser Tyr Gln Ser Ser Ser
 1               5

(2) INFORMATION FOR SEQ ID NO:20:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Lys Tyr Gln Ser Ser Ser
 1               5

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine (xi) SEQUENCE DESCRIPTION: SEQ ID NO:21:

Xaa Tyr Gln Ser Ser Ser
 1               5

(2) INFORMATION FOR SEQ ID NO:22:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:22:

Ser Tyr Gln Ser Ser Leu
 1               5

(2) INFORMATION FOR SEQ ID NO:23:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (xi) SEQUENCE DESCRIPTION: SEQ ID NO:23:

Ser Tyr Gln Ser Leu
 1               5

(2) INFORMATION FOR SEQ ID NO:24:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Other
           (B) LOCATION: 2...2
           (D) OTHER INFORMATION: Cyclohexylglycine (xi) SEQUENCE DESCRIPTION: SEQ ID NO:24:

Ser Xaa Gln Ser Leu
 1               5

(2) INFORMATION FOR SEQ ID NO:25:

(i) SEQUENCE CHARACTERISTICS:
           (A) LENGTH: 5 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Other
           (B) LOCATION: 1...1
           (D) OTHER INFORMATION: Homoarginine
           (A) NAME/KEY: Other
           (B) LOCATION: 2...2
           (D) OTHER INFORMATION: Cyclohexylglycine (xi) SEQUENCE DESCRIPTION: SEQ ID NO:25:

```
Xaa Xaa Gln Ser Leu
 1           5
```

(2) INFORMATION FOR SEQ ID NO:26:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine (xi) SEQUENCE DESCRIPTION: SEQ ID NO:26:

```
Xaa Tyr Gln Ser Leu
 1           5
```

(2) INFORMATION FOR SEQ ID NO:27:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:27:

```
Gly Glu Asn Gly Val Gln Lys Asp Val Ser Gln Arg Ser Ile Tyr Ser
 1               5                  10                  15

Gln Thr Glu
```

(2) INFORMATION FOR SEQ ID NO:28:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:28:

```
Ala Ser Tyr Gln Ser Ser Leu
 1           5
```

(2) INFORMATION FOR SEQ ID NO:29:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine (xi) SEQUENCE DESCRIPTION: SEQ ID NO:29:

```
Ser Xaa Xaa Gln Ser Leu
```

-continued (2) INFORMATION FOR SEQ ID NO:30:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine
        (A) NAME/KEY: Other
        (B) LOCATION: 7...7
        (D) OTHER INFORMATION: Norleucine (xi) SEQUENCE DESCRIPTION: SEQ ID NO:30:

Xaa Ser Ser Tyr Gln Ser Leu
1           5

(2) INFORMATION FOR SEQ ID NO:31:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine
        (A) NAME/KEY: Other
        (B) LOCATION: 4...4
        (D) OTHER INFORMATION: Cyclohexylglycine (xi) SEQUENCE DESCRIPTION: SEQ ID NO:31:

Xaa Ala Ser Xaa Gln Ser Leu
1           5

(2) INFORMATION FOR SEQ ID NO:32:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine (xi) SEQUENCE DESCRIPTION: SEQ ID NO:32:

Xaa Ser Ser Tyr Gln Ser Leu
1           5

(2) INFORMATION FOR SEQ ID NO:33:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
              (A) NAME/KEY: Other
              (B) LOCATION: 1...1
              (D) OTHER INFORMATION: Homoarginine
              (A) NAME/KEY: Other
              (B) LOCATION: 4...4
              (D) OTHER INFORMATION: Cyclohexylglycine (xi) SEQUENCE DESCRIPTION: SEQ ID NO:33:

Xaa Ser Ser Xaa Ser Leu
 1               5

(2) INFORMATION FOR SEQ ID NO:34:

(i) SEQUENCE CHARACTERISTICS:
              (A) LENGTH: 6 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 2...2
              (D) OTHER INFORMATION: Homoarginine
              (A) NAME/KEY: Other
              (B) LOCATION: 3...3
              (D) OTHER INFORMATION: Cyclohexylglycine (xi) SEQUENCE DESCRIPTION: SEQ ID NO:34:

Ser Xaa Xaa Gln Ser Leu
 1               5

(2) INFORMATION FOR SEQ ID NO:35:

(i) SEQUENCE CHARACTERISTICS:
              (A) LENGTH: 5 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: Homoarginine (xi) SEQUENCE DESCRIPTION: SEQ ID NO:35:

Xaa Tyr Gln Ser Leu
 1               5

(2) INFORMATION FOR SEQ ID NO:36:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: Homoarginine
              (A) NAME/KEY: Other
              (B) LOCATION: 4...4
              (D) OTHER INFORMATION: Cyclohexylglycine (xi) SEQUENCE DESCRIPTION: SEQ ID NO:36:

Xaa Ser Ser Xaa Gln Ser Leu
 1               5

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2...2
        (D) OTHER INFORMATION: Homoarginine (xi) SEQUENCE DESCRIPTION: SEQ ID NO:37:

Ser Xaa Tyr Gln Ser Leu
 1           5

(2) INFORMATION FOR SEQ ID NO:38:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Ser Ser Tyr Gln Ser Leu
 1           5

(2) INFORMATION FOR SEQ ID NO:39:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 4...4
        (D) OTHER INFORMATION: Cyclohexylglycine (xi) SEQUENCE DESCRIPTION: SEQ ID NO:39:

Ser Ser Ser Xaa Gln Ser Leu
 1               5

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: 3-Pyridylalanine
        (A) NAME/KEY: Other
        (B) LOCATION: 4...4
        (D) OTHER INFORMATION: Cyclohexylglycine (xi) SEQUENCE DESCRIPTION: SEQ ID NO:40:

Xaa Ser Ser Xaa Gln Ser Leu
1               5

(2) INFORMATION FOR SEQ ID NO:41:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 3...3
        (D) OTHER INFORMATION: Cyclohexylglycine (xi) SEQUENCE DESCRIPTION: SEQ ID NO:41:

Ser Ser Xaa Gln Ser Leu
1               5

(2) INFORMATION FOR SEQ ID NO:42:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 3...3
        (D) OTHER INFORMATION: Cyclohexylglycine
        (A) NAME/KEY: Other
        (B) LOCATION: 7...7
        (D) OTHER INFORMATION: Leucine with Unnatural
            Stereoconfiguration (xi) SEQUENCE DESCRIPTION: SEQ ID NO:42:

Ser Ser Ser Xaa Gln Ser Xaa
1               5

(2) INFORMATION FOR SEQ ID NO:43:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 4...4
        (D) OTHER INFORMATION: Cyclohexylglycine (xi) SEQUENCE DESCRIPTION: SEQ ID NO:43:

Ser Ser Ser Xaa Gln Ser Val
1               5

(2) INFORMATION FOR SEQ ID NO:44:

(i) SEQUENCE CHARACTERISTICS:
        (A) LENGTH: 7 amino acids
        (B) TYPE: amino acid
        (C) STRANDEDNESS: single (D) TOPOLOGY: linear (ii) MOLECULE TYPE: peptide (ix) FEATURE:
          (A) NAME/KEY: Other
          (B) LOCATION: 4...4
          (D) OTHER INFORMATION: Cyclohexylglycine (xi) SEQUENCE DESCRIPTION: SEQ ID NO:44:

Pro Ser Ser Xaa Gln Ser Val
 1               5

(2) INFORMATION FOR SEQ ID NO:45:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Other
          (B) LOCATION: 4...4
          (D) OTHER INFORMATION: Cyclohexylglycine (xi) SEQUENCE DESCRIPTION: SEQ ID NO:45:

Gly Ser Ser Xaa Gln Ser Leu
 1               5

(2) INFORMATION FOR SEQ ID NO:46:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Other
          (B) LOCATION: 1...1
          (D) OTHER INFORMATION: Homoserine
          (A) NAME/KEY: Other
          (B) LOCATION: 4...4
          (D) OTHER INFORMATION: Cyclohexylglycine (xi) SEQUENCE DESCRIPTION: SEQ ID NO:46:

Xaa Ser Ser Xaa Gln Ser Leu
 1               5

(2) INFORMATION FOR SEQ ID NO:47:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Other
          (B) LOCATION: 1...1
          (D) OTHER INFORMATION: Homoarginine
          (A) NAME/KEY: Other
          (B) LOCATION: 4...4
          (D) OTHER INFORMATION: Cyclohexylglycine
          (A) NAME/KEY: Other
          (B) LOCATION: 7...7
          (D) OTHER INFORMATION: Norleucine (xi) SEQUENCE DESCRIPTION: SEQ ID NO:47:

Xaa Ser Ser Xaa Gln Ser Leu
1               5

(2) INFORMATION FOR SEQ ID NO:48:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine
        (A) NAME/KEY: Other
        (B) LOCATION: 4...4
        (D) OTHER INFORMATION: Cyclohexylglycine (xi) SEQUENCE DESCRIPTION: SEQ ID NO:48:

Xaa Ser Ala Xaa Gln Ser Leu
1               5

(2) INFORMATION FOR SEQ ID NO:49:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

Asn Arg Ile Ser Tyr Gln Ser
1               5

(2) INFORMATION FOR SEQ ID NO:50:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

Asn Lys Val Ser Tyr Gln Ser
1               5

(2) INFORMATION FOR SEQ ID NO:51:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:51:

Asn Lys Met Ser Tyr Gln Ser Ser
1               5

(2) INFORMATION FOR SEQ ID NO:52:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:52:

Asn Lys Leu Ser Tyr Gln Ser Ser
1               5

(2) INFORMATION FOR SEQ ID NO:53:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

Asn Lys Ile Ser Tyr Gln Ser
1               5

(2) INFORMATION FOR SEQ ID NO:54:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:54:

Gln Lys Ile Ser Tyr Gln Ser Ser
1               5

(2) INFORMATION FOR SEQ ID NO:55:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Homoarginine (xi) SEQUENCE DESCRIPTION: SEQ ID NO:55:

Xaa Tyr Gln Ser Ser Ser Leu
1               5

(2) INFORMATION FOR SEQ ID NO:56:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:56:

```
Lys Tyr Gln Ser Ser Ser Leu
1               5

(2) INFORMATION FOR SEQ ID NO:57:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:57:

Ser Tyr Gln Ser Ser Ser Leu
1               5

(2) INFORMATION FOR SEQ ID NO:58:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 3...3
        (D) OTHER INFORMATION: Cyclohexylglycine
        (A) NAME/KEY: Other
        (B) LOCATION: 6...6
        (D) OTHER INFORMATION: Leucine with Unnatural
            Stereoconfiguration (xi) SEQUENCE DESCRIPTION: SEQ ID NO:58:

Ser Ser Xaa Gln Ser Xaa
1               5

(2) INFORMATION FOR SEQ ID NO:59:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Pyridylalanine
        (A) NAME/KEY: Other
        (B) LOCATION: 4...4
        (D) OTHER INFORMATION: Cyclohexylglycine
        (A) NAME/KEY: Other
        (B) LOCATION: 7...7
        (D) OTHER INFORMATION: Leucine with Unnatural
            Stereoconfiguration (xi) SEQUENCE DESCRIPTION: SEQ ID NO:59:

Xaa Ser Ser Xaa Gln Ser Xaa
1               5

(2) INFORMATION FOR SEQ ID NO:60:

(i) SEQUENCE CHARACTERISTICS:
        (A) LENGTH: 6 amino acids
        (B) TYPE: amino acid
        (C) STRANDEDNESS: single
        (D) TOPOLOGY: linear
```

(ii) MOLECULE TYPE: peptide (ix) FEATURE:
              (A) NAME/KEY: Other
              (B) LOCATION: 3...3
              (D) OTHER INFORMATION: Cyclohexylglycine (xi) SEQUENCE DESCRIPTION: SEQ ID NO:60:

Ala Ser Xaa Gln Ser Leu
 1               5

(2) INFORMATION FOR SEQ ID NO:61:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: N-(2-Hydroxyacetyl)Serine
              (A) NAME/KEY: Other
              (B) LOCATION: 4...4
              (D) OTHER INFORMATION: Cyclohexylglycine (xi) SEQUENCE DESCRIPTION: SEQ ID NO:61:

Xaa Ser Ser Xaa Gln Ser Leu
 1               5

(2) INFORMATION FOR SEQ ID NO:62:

(i) SEQUENCE CHARACTERISTICS:
              (A) LENGTH: 6 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: N-(2-Hydroxyacetyl)Serine
              (A) NAME/KEY: Other
              (B) LOCATION: 3...3
              (D) OTHER INFORMATION: Cyclohexylglycine (xi) SEQUENCE DESCRIPTION: SEQ ID NO:62:

Xaa Ser Xaa Gln Ser Leu
 1               5

(2) INFORMATION FOR SEQ ID NO:63:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: N-(PEG-2)Serine
              (A) NAME/KEY: Other
              (B) LOCATION: 4...4
              (D) OTHER INFORMATION: Cyclohexylglycine (xi) SEQUENCE DESCRIPTION: SEQ ID NO:63:

Xaa Ser Ser Xaa Gln Ser Leu
1               5

(2) INFORMATION FOR SEQ ID NO:64:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2-Hydroxyacetyl)Homoarginine
        (A) NAME/KEY: Other
        (B) LOCATION: 7...7
        (D) OTHER INFORMATION: Norleucine (xi) SEQUENCE DESCRIPTION: SEQ ID NO:64:

Xaa Ser Ser Tyr Gln Ser Leu
1               5

(2) INFORMATION FOR SEQ ID NO:65:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2-Hydroxyacetyl)Homoarginine
        (A) NAME/KEY: Other
        (B) LOCATION: 4...4
        (D) OTHER INFORMATION: Cyclohexylglycine
        (A) NAME/KEY: Other
        (B) LOCATION: 7...7
        (D) OTHER INFORMATION: Norleucine (xi) SEQUENCE DESCRIPTION: SEQ ID NO:65:

Xaa Ser Ser Xaa Gln Ser Leu
1               5

(2) INFORMATION FOR SEQ ID NO:66:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2-Hydroxyacetyl)Serine
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine (xi) SEQUENCE DESCRIPTION: SEQ ID NO:66:

Xaa Xaa Xaa Gln Ser Leu
1           5

(2) INFORMATION FOR SEQ ID NO:67:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2-Hydroxyacetyl)Homoarginine
        (A) NAME/KEY: Other
        (B) LOCATION: 4...4
        (D) OTHER INFORMATION: Cyclohexylglycine (xi) SEQUENCE DESCRIPTION: SEQ ID NO:67:

Xaa Ser Ser Xaa Gln Ser Leu
1           5

(2) INFORMATION FOR SEQ ID NO:68:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2-Hydroxyacetyl)Homoarginine
        (A) NAME/KEY: Other
        (B) LOCATION: 4...4
        (D) OTHER INFORMATION: Cyclohexylglycine (xi) SEQUENCE DESCRIPTION: SEQ ID NO:68:

Xaa Ala Ser Xaa Gln Ser Leu
1           5

(2) INFORMATION FOR SEQ ID NO:69:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-((d)-2,3-Dihydroxypropionyl)Serine
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine (xi) SEQUENCE DESCRIPTION: SEQ ID NO:69:

Xaa Xaa Xaa Gln Ser Leu
1           5

(2) INFORMATION FOR SEQ ID NO:70:

```
    (i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-((1)-2,3-Dihydroxypropionyl)Serine
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine (xi) SEQUENCE DESCRIPTION: SEQ ID NO:70:

Xaa Xaa Xaa Gln Ser Leu
 1               5

(2) INFORMATION FOR SEQ ID NO:71:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Serine
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine (xi) SEQUENCE DESCRIPTION: SEQ ID NO:71:

Xaa Xaa Xaa Gln Ser Leu
 1               5

(2) INFORMATION FOR SEQ ID NO:72:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Homoarginine
        (A) NAME/KEY: Other
        (B) LOCATION: 2...2
        (D) OTHER INFORMATION: Cyclohexylglycine (xi) SEQUENCE DESCRIPTION: SEQ ID NO:72:

Xaa Xaa Gln Ser Leu
 1           5

(2) INFORMATION FOR SEQ ID NO:73:

(i) SEQUENCE CHARACTERISTICS:
```

(A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: N-((2R,3S)-2,3,4-Trihydroxybutanoyl)
                    Homoarginine
            (A) NAME/KEY: Other
            (B) LOCATION: 2...2
            (D) OTHER INFORMATION: Cyclohexylglycine (xi) SEQUENCE DESCRIPTION: SEQ ID NO:73:

Xaa Xaa Gln Ser Leu
 1               5

(2) INFORMATION FOR SEQ ID NO:74:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: N-(PEG-2)Serine
            (A) NAME/KEY: Other
            (B) LOCATION: 2...2
            (D) OTHER INFORMATION: Homoarginine (xi) SEQUENCE DESCRIPTION: SEQ ID NO:74:

Xaa Xaa Tyr Gln Ser Leu
 1               5

(2) INFORMATION FOR SEQ ID NO:75:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: N-(PEG-2)Homoarginine (xi) SEQUENCE DESCRIPTION: SEQ ID NO:75:

Xaa Tyr Gln Ser Ser Ser Leu
 1               5

(2) INFORMATION FOR SEQ ID NO:76:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1

(D) OTHER INFORMATION: N-(PEG-2)Lysine (xi) SEQUENCE DESCRIPTION: SEQ ID NO:76:

Xaa Tyr Gln Ser Ser Ser Leu
 1               5

(2) INFORMATION FOR SEQ ID NO:77:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2-Hydroxyacetyl)Homoarginine (xi) SEQUENCE DESCRIPTION: SEQ ID NO:77:

Xaa Ser Ser Tyr Gln Ser Leu
 1               5

(2) INFORMATION FOR SEQ ID NO:78:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-((1)-2,3-Dihydroxypropionyl)
             Homoarginine
        (A) NAME/KEY: Other
        (B) LOCATION: 4...4
        (D) OTHER INFORMATION: Cyclohexylglycine (xi) SEQUENCE DESCRIPTION: SEQ ID NO:78:

Xaa Ser Ser Xaa Gln Ser Leu
 1               5

(2) INFORMATION FOR SEQ ID NO:79:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Homoarginine
        (A) NAME/KEY: Other
        (B) LOCATION: 4...4
        (D) OTHER INFORMATION: Cyclohexylglycine (xi) SEQUENCE DESCRIPTION: SEQ ID NO:79:

Xaa Ser Ser Xaa Gln Ser Leu
 1               5

(2) INFORMATION FOR SEQ ID NO:80:

```
    (i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2-Hydroxyacetyl)Serine (xi) SEQUENCE DESCRIPTION: SEQ ID NO:80:

Xaa Tyr Gln Ser Ser Ser Leu
 1               5

(2) INFORMATION FOR SEQ ID NO:81:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-16)Serine
        (A) NAME/KEY: Other
        (B) LOCATION: 2...2
        (D) OTHER INFORMATION: Homoarginine (xi) SEQUENCE DESCRIPTION: SEQ ID NO:81:

Xaa Xaa Tyr Gln Ser Leu
 1               5

(2) INFORMATION FOR SEQ ID NO:82:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-((2R,3S)-2,3,4-Trihydroxybutanoyl)
              Serine
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine (xi) SEQUENCE DESCRIPTION: SEQ ID NO:82:

Xaa Xaa Xaa Gln Ser Leu
 1               5

(2) INFORMATION FOR SEQ ID NO:83:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide
```

(ix) FEATURE:
              (A) NAME/KEY: Other
              (B) LOCATION: 1...1
              (D) OTHER INFORMATION: N-(PEG-2)Serine
              (A) NAME/KEY: Other
              (B) LOCATION: 2...2
              (D) OTHER INFORMATION: Homoarginine (xi) SEQUENCE DESCRIPTION: SEQ ID NO:83:

Xaa Xaa Tyr Gln Ser Leu
 1               5

(2) INFORMATION FOR SEQ ID NO:84:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: N-(d)-2,3-Dihydroxypropionyl)
                  Homoarginine
              (A) NAME/KEY: Other
              (B) LOCATION: 4...4
              (D) OTHER INFORMATION: Cyclohexylglycine (xi) SEQUENCE DESCRIPTION: SEQ ID NO:84:

Xaa Ser Ser Xaa Gln Ser Leu
 1               5

(2) INFORMATION FOR SEQ ID NO:85:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other
              (B) LOCATION: 1...1
              (D) OTHER INFORMATION: N-((1)-2,3-Dihydroxypropionyl)Serine
              (A) NAME/KEY: Other
              (B) LOCATION: 4...4
              (D) OTHER INFORMATION: Cyclohexylglycine
              (A) NAME/KEY: Other
              (B) LOCATION: 7...7
              (D) OTHER INFORMATION: Leucine with Unnatural
                  Stereoconfiguration (xi) SEQUENCE DESCRIPTION: SEQ ID NO:85:

Xaa Ser Ser Xaa Gln Ser Xaa
 1               5

(2) INFORMATION FOR SEQ ID NO:86:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Other (B) LOCATION: 1...1
            (D) OTHER INFORMATION: N-((d)-2,3-Dihydroxypropionyl)Serine
            (A) NAME/KEY: Other
            (B) LOCATION: 4...4
            (D) OTHER INFORMATION: Cyclohexylglycine (xi) SEQUENCE DESCRIPTION: SEQ ID NO:86:

Xaa Ser Ser Xaa Gln Ser Leu
 1               5

(2) INFORMATION FOR SEQ ID NO:87:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (B) LOCATION: 1...1
         (D) OTHER INFORMATION: N-((1)-2,3-Dihydroxypropionyl)Serine
         (A) NAME/KEY: Other
         (B) LOCATION: 4...4
         (D) OTHER INFORMATION: Cyclohexylglycine (xi) SEQUENCE DESCRIPTION: SEQ ID NO:87:

Xaa Ser Ser Xaa Gln Ser Leu
 1               5

(2) INFORMATION FOR SEQ ID NO:88:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (B) LOCATION: 1...1
         (D) OTHER INFORMATION: N-((1)-2,3-Dihydroxypropionyl)Serine
         (A) NAME/KEY: Other
         (B) LOCATION: 3...3
         (D) OTHER INFORMATION: Cyclohexylglycine
         (A) NAME/KEY: Other
         (B) LOCATION: 6...6
         (D) OTHER INFORMATION: Leucine with Unnatural
             Stereoconfiguration (xi) SEQUENCE DESCRIPTION: SEQ ID NO:88:

Xaa Ser Xaa Gln Ser Xaa
 1               5

(2) INFORMATION FOR SEQ ID NO:89:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Other
         (B) LOCATION: 1...1
         (D) OTHER INFORMATION: N-((d)-2,3-Dihydroxypropionyl)Serine
         (A) NAME/KEY: Other
         (B) LOCATION: 3...3

(D) OTHER INFORMATION: Cyclohexylglycine (xi) SEQUENCE DESCRIPTION: SEQ ID NO:89:

Xaa Ser Xaa Gln Ser Leu
 1               5

(2) INFORMATION FOR SEQ ID NO:90:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Serine
        (A) NAME/KEY: Other
        (B) LOCATION: 3...3
        (D) OTHER INFORMATION: Cyclohexylglycine
        (A) NAME/KEY: Other
        (B) LOCATION: 6...6
        (D) OTHER INFORMATION: Leucine with Unnatural
            Stereoconfiguration (xi) SEQUENCE DESCRIPTION: SEQ ID NO:90:

Xaa Ser Xaa Gln Ser Xaa
 1               5

(2) INFORMATION FOR SEQ ID NO:91:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Serine
        (A) NAME/KEY: Other
        (B) LOCATION: 3...3
        (D) OTHER INFORMATION: Cyclohexylglycine (xi) SEQUENCE DESCRIPTION: SEQ ID NO:91:

Xaa Ser Xaa Gln Ser Leu
 1               5

(2) INFORMATION FOR SEQ ID NO:92:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Serine
        (A) NAME/KEY: Other
        (B) LOCATION: 4...4
        (D) OTHER INFORMATION: Cyclohexylglycine
        (A) NAME/KEY: Other
        (B) LOCATION: 7...7
        (D) OTHER INFORMATION: Leucine with Unnatural Stereoconfiguration (xi) SEQUENCE DESCRIPTION: SEQ ID NO:92:

Xaa Ser Ser Xaa Gln Ser Xaa
 1               5

(2) INFORMATION FOR SEQ ID NO:93:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2,3-Dihydroxypropionyl)
            -3-Pyridylalanine
        (A) NAME/KEY: Other
        (B) LOCATION: 4...4
        (D) OTHER INFORMATION: Cyclohexylglycine
        (A) NAME/KEY: Other
        (B) LOCATION: 7...7
        (D) OTHER INFORMATION: Leucine with Unnatural
            Stereoconfiguration (xi) SEQUENCE DESCRIPTION: SEQ ID NO:93:

Xaa Ser Ser Xaa Gln Ser Xaa
 1               5

(2) INFORMATION FOR SEQ ID NO:94:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-((d)-2,3-Dihydroxypropionyl)
            -3-Pyridylalanine
        (A) NAME/KEY: Other
        (B) LOCATION: 4...4
        (D) OTHER INFORMATION: Cyclohexylglycine (xi) SEQUENCE DESCRIPTION: SEQ ID NO:94:

Xaa Ser Ser Xaa Gln Ser Leu
 1               5

(2) INFORMATION FOR SEQ ID NO:95:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-((1)-2,3-Dihydroxypropionyl)Serine
        (A) NAME/KEY: Other
        (B) LOCATION: 4...4
        (D) OTHER INFORMATION: Cyclohexylglycine (xi) SEQUENCE DESCRIPTION: SEQ ID NO:95:

Xaa Ser Xaa Gln Ser Leu
 1               5

(2) INFORMATION FOR SEQ ID NO:96:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(2,3-Dihydroxypropionyl)Homoserine
        (A) NAME/KEY: Other
        (B) LOCATION: 4...4
        (D) OTHER INFORMATION: Cyclohexylglycine (xi) SEQUENCE DESCRIPTION: SEQ ID NO:96:

Xaa Ser Ser Xaa Gln Ser Leu
 1               5

(2) INFORMATION FOR SEQ ID NO:97:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Alanine
        (A) NAME/KEY: Other
        (B) LOCATION: 3...3
        (D) OTHER INFORMATION: Cyclohexylglycine (xi) SEQUENCE DESCRIPTION: SEQ ID NO:97:

Xaa Ser Xaa Gln Ser Leu
 1               5

(2) INFORMATION FOR SEQ ID NO:98:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-6)Serine
        (A) NAME/KEY: Other
        (B) LOCATION: 3...3
        (D) OTHER INFORMATION: Cyclohexylglycine (xi) SEQUENCE DESCRIPTION: SEQ ID NO:98:

Xaa Ser Xaa Gln Ser Leu
 1               5

(2) INFORMATION FOR SEQ ID NO:99:

```
    (i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-6)Serine
        (A) NAME/KEY: Other
        (B) LOCATION: 4...4
        (D) OTHER INFORMATION: Cyclohexylglycine (xi) SEQUENCE DESCRIPTION: SEQ ID NO:99:

Xaa Ser Ser Xaa Gln Ser Leu
 1               5

(2) INFORMATION FOR SEQ ID NO:100:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-6)Alanine
        (A) NAME/KEY: Other
        (B) LOCATION: 3...3
        (D) OTHER INFORMATION: Cyclohexylglycine (xi) SEQUENCE DESCRIPTION: SEQ ID NO:100:

Xaa Ser Xaa Gln Ser Leu
 1           5

(2) INFORMATION FOR SEQ ID NO:101:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-4)-3-Pyridylalanine
        (A) NAME/KEY: Other
        (B) LOCATION: 4...4
        (D) OTHER INFORMATION: Cyclohexylglycine (xi) SEQUENCE DESCRIPTION: SEQ ID NO:101:

Xaa Ser Ser Xaa Gln Ser Leu
 1               5

(2) INFORMATION FOR SEQ ID NO:102:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide
```

(ix) FEATURE:
            (A) NAME/KEY: Other
            (B) LOCATION: 4...4
            (D) OTHER INFORMATION: Cyclohexylglycine
            (A) NAME/KEY: Other
            (B) LOCATION: 7...7
            (D) OTHER INFORMATION: Leucine-2-Hydroxyethylamine (xi) SEQUENCE DESCRIPTION: SEQ ID NO:102:

Ser Ser Ser Xaa Gln Ser Xaa
1               5

(2) INFORMATION FOR SEQ ID NO:103:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: N-Acetylalanine (xi) SEQUENCE DESCRIPTION: SEQ ID NO:103:

Xaa Arg Lys Ala Ser Tyr Gln Ser Leu
1               5

(2) INFORMATION FOR SEQ ID NO:104:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: N-Acetylalanine (xi) SEQUENCE DESCRIPTION: SEQ ID NO:104:

Xaa Arg Lys Ala Ser Tyr Gln Ser Leu
1               5

(2) INFORMATION FOR SEQ ID NO:105:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Other
            (B) LOCATION: 1...1
            (D) OTHER INFORMATION: N-Acetylhomoarginine
            (A) NAME/KEY: Other
            (B) LOCATION: 2...2
            (D) OTHER INFORMATION: Cyclohexylalanine
            (A) NAME/KEY: Other
            (B) LOCATION: 5...5
            (D) OTHER INFORMATION: Norleucine (xi) SEQUENCE DESCRIPTION: SEQ ID NO:105:

Xaa Xaa Gln Ser Leu (2) INFORMATION FOR SEQ ID NO:106:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-Acetylserine
        (A) NAME/KEY: Other
        (B) LOCATION: 2...2
        (D) OTHER INFORMATION: Homoarginine
        (A) NAME/KEY: Other
        (B) LOCATION: 6...6
        (D) OTHER INFORMATION: Norleucine (xi) SEQUENCE DESCRIPTION: SEQ ID NO:106:

Xaa Xaa Tyr Gln Ser Leu
 1               5

(2) INFORMATION FOR SEQ ID NO:107:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine
        (A) NAME/KEY: Other
        (B) LOCATION: 6...6
        (D) OTHER INFORMATION: Norleucine (xi) SEQUENCE DESCRIPTION: SEQ ID NO:107:

Ser Xaa Xaa Gln Ser Leu
 1               5

(2) INFORMATION FOR SEQ ID NO:108:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-Acetylhomoarginine
        (A) NAME/KEY: Other
        (B) LOCATION: 7...7
        (D) OTHER INFORMATION: Norleucine (xi) SEQUENCE DESCRIPTION: SEQ ID NO:108:

Xaa Ser Ser Tyr Gln Ser Leu
 1               5

(2) INFORMATION FOR SEQ ID NO:109:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-Acetylhomoarginine
        (A) NAME/KEY: Other
        (B) LOCATION: 4...4
        (D) OTHER INFORMATION: Cyclohexylglycine (xi) SEQUENCE DESCRIPTION: SEQ ID NO:109:

Xaa Ser Ser Xaa Gln Ser Leu
 1               5

(2) INFORMATION FOR SEQ ID NO:110:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-Acetylhomoarginine
        (A) NAME/KEY: Other
        (B) LOCATION: 7...7
        (D) OTHER INFORMATION: Norleucine (xi) SEQUENCE DESCRIPTION: SEQ ID NO:110:

Xaa Ser Ser Tyr Gln Ser Leu
 1               5

(2) INFORMATION FOR SEQ ID NO:111:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-Acetylhomoarginine
        (A) NAME/KEY: Other
        (B) LOCATION: 4...4
        (D) OTHER INFORMATION: Cyclohexylglycine (xi) SEQUENCE DESCRIPTION: SEQ ID NO:111:

Xaa Ala Ser Xaa Gln Ser Leu
 1               5

(2) INFORMATION FOR SEQ ID NO:112:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Other
    (B) LOCATION: 1...1
    (D) OTHER INFORMATION: N-(2-Hydroxyacetyl)Homoarginine (xi) SEQUENCE DESCRIPTION: SEQ ID NO:112:

Xaa Tyr Gln Ser Leu
 1                5

(2) INFORMATION FOR SEQ ID NO:113:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-1)Serine
        (A) NAME/KEY: Other
        (B) LOCATION: 2...2
        (D) OTHER INFORMATION: Homoarginine
        (A) NAME/KEY: Other
        (B) LOCATION: 3...3
        (D) OTHER INFORMATION: Cyclohexylglycine (xi) SEQUENCE DESCRIPTION: SEQ ID NO:113:

Xaa Xaa Xaa Gln Ser Leu
 1                5

(2) INFORMATION FOR SEQ ID NO:114:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-1)Homoarginine
        (A) NAME/KEY: Other
        (B) LOCATION: 4...4
        (D) OTHER INFORMATION: Cyclohexylglycine (xi) SEQUENCE DESCRIPTION: SEQ ID NO:114:

Xaa Ser Ser Xaa Gln Ser Leu
 1                5

(2) INFORMATION FOR SEQ ID NO:115:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-1)Serine
        (A) NAME/KEY: Other (B) LOCATION: 2...2
            (D) OTHER INFORMATION: Homoarginine (xi) SEQUENCE DESCRIPTION: SEQ ID NO:115:

Xaa Xaa Tyr Gln Ser Leu
1               5

(2) INFORMATION FOR SEQ ID NO:116:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-15)Serine
        (A) NAME/KEY: Other
        (B) LOCATION: 2...2
        (D) OTHER INFORMATION: Homoarginine (xi) SEQUENCE DESCRIPTION: SEQ ID NO:116:

Xaa Xaa Tyr Gln Ser Leu
1               5

(2) INFORMATION FOR SEQ ID NO:117:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-17)Serine
        (A) NAME/KEY: Other
        (B) LOCATION: 2...2
        (D) OTHER INFORMATION: Homoarginine (xi) SEQUENCE DESCRIPTION: SEQ ID NO:117:

Xaa Xaa Tyr Gln Ser Leu
1               5

(2) INFORMATION FOR SEQ ID NO:118:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-2)Serine (xi) SEQUENCE DESCRIPTION: SEQ ID NO:118:

Xaa Ser Tyr Gln Ser Leu
1               5

(2) INFORMATION FOR SEQ ID NO:119:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-14)Serine
        (A) NAME/KEY: Other
        (B) LOCATION: 2...2
        (D) OTHER INFORMATION: Homoarginine (xi) SEQUENCE DESCRIPTION: SEQ ID NO:119:

Xaa Xaa Tyr Gln Ser Leu
 1               5

(2) INFORMATION FOR SEQ ID NO:120:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-18)Serine
        (A) NAME/KEY: Other
        (B) LOCATION: 2...2
        (D) OTHER INFORMATION: Homoarginine (xi) SEQUENCE DESCRIPTION: SEQ ID NO:120:

Xaa Xaa Tyr Gln Ser Leu
 1               5

(2) INFORMATION FOR SEQ ID NO:121:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: N-(PEG-19)Serine
        (A) NAME/KEY: Other
        (B) LOCATION: 2...2
        (D) OTHER INFORMATION: Homoarginine (xi) SEQUENCE DESCRIPTION: SEQ ID NO:121:

Xaa Xaa Tyr Gln Ser Leu
 1               5

(2) INFORMATION FOR SEQ ID NO:122:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Other
         (B) LOCATION: 1...1
         (D) OTHER INFORMATION: N-((1)-2,3-Dihydroxypropionyl)Serine
         (A) NAME/KEY: Other
         (B) LOCATION: 3...3
         (D) OTHER INFORMATION: Cyclohexylglycine (xi) SEQUENCE DESCRIPTION: SEQ ID NO:122:

Xaa Ser Xaa Gln Ser Leu
1               5

(2) INFORMATION FOR SEQ ID NO:123:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 1...1
         (D) OTHER INFORMATION: N-((1)-2,3-Dihydroxypropionyl)
             -3-Pyridylalanine
         (A) NAME/KEY: Other
         (B) LOCATION: 4...4
         (D) OTHER INFORMATION: Cyclohexylglycine (xi) SEQUENCE DESCRIPTION: SEQ ID NO:123:

Xaa Ser Ser Xaa Gln Ser Leu
1               5

(2) INFORMATION FOR SEQ ID NO:124:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 1...1
         (D) OTHER INFORMATION: N-(2,3-Dihydroxypropionyl)Serine
         (A) NAME/KEY: Other
         (B) LOCATION: 4...4
         (D) OTHER INFORMATION: Cyclohexylglycine (xi) SEQUENCE DESCRIPTION: SEQ ID NO:124:

Xaa Ser Ser Xaa Gln Ser Leu
1               5

(2) INFORMATION FOR SEQ ID NO:125:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
         (A) NAME/KEY: Other
         (B) LOCATION: 1...1
         (D) OTHER INFORMATION: N-(2,3-Dihydroxypropionyl)Serine
         (A) NAME/KEY: Other
         (B) LOCATION: 2...2
         (D) OTHER INFORMATION: Homoarginine
```

(xi) SEQUENCE DESCRIPTION: SEQ ID NO:125:

Xaa Xaa Tyr Gln Ser Leu
1               5

(2) INFORMATION FOR SEQ ID NO:126:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Other
          (B) LOCATION: 1...1
          (D) OTHER INFORMATION: N-acetylserine
          (A) NAME/KEY: Other
          (B) LOCATION: 4...4
          (D) OTHER INFORMATION: Cyclohexylglycine (xi) SEQUENCE DESCRIPTION: SEQ ID NO:126:

Xaa Ser Ser Xaa Gln Ser Val
1               5

(2) INFORMATION FOR SEQ ID NO:127:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Other
          (B) LOCATION: 1...1
          (D) OTHER INFORMATION: N-Acetylproline
          (A) NAME/KEY: Other
          (B) LOCATION: 4...4
          (D) OTHER INFORMATION: Cyclohexylglycine (xi) SEQUENCE DESCRIPTION: SEQ ID NO:127:

Xaa Ser Ser Xaa Gln Ser Val
1               5

(2) INFORMATION FOR SEQ ID NO:128:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Other
          (B) LOCATION: 1...1
          (D) OTHER INFORMATION: N-(2,3-Dihydroxypropionyl)Glycine
          (A) NAME/KEY: Other
          (B) LOCATION: 4...4
          (D) OTHER INFORMATION: Cyclohexylglycine (xi) SEQUENCE DESCRIPTION: SEQ ID NO:128:

Xaa Ser Ser Xaa Gln Ser Leu
1               5

CONJUGATES USEFUL IN THE TREATMENT OF PROSTATE CANCER

This application claims priority to 60/026,015 filed Sep. 12, 1996.

BACKGROUND OF THE INVENTION

In 1994 cancer of the prostate gland is expected to be diagnosed in 200,000 men in the U.S. and 38,000 American males will die from this disease (Garnick, M. B. (1994). The Dilemmas of Prostate Cancer. Scientific American, April:72–81). Thus, prostate cancer is the most frequently diagnosed malignancy (other than that of the skin) in U.S. men and the second leading cause of cancer-related deaths (behind lung cancer) in that group.

Prostate specific Antigen (PSA) is a single chain 33 kDa glycoprotein that is produced almost exclusively by the human prostate epithelium and occurs at levels of 0.5 to 2.0 mg/ml in human seminal fluid (Nadji, M., Taber, S. Z., Castro, A., et al. (1981) Cancer 48:1229; Papsidero, L., Kuriyama, M., Wang, M., et al. (1981). JNCI 66:37; Qui, S. D., Young, C. Y. F., Bihartz, D. L., et al. (1990), J. Urol. 144:1550; Wang, M. C., Valenzuela, L. A., Murphy, G. P., et al. (1979). Invest. Urol. 17:159). The single carbohydrate unit is attached at asparagine residue number 45 and accounts for 2 to 3 kDa of the total molecular mass. PSA is a protease with chymotrypsin-like specificity (Christensson, A., Laurell, C. B., Lilja, H. (1990). Eur. J. Biochem. 194:755–763). It has been shown that PSA is mainly responsible for dissolution of the gel structure formed at ejaculation by proteolysis of the major proteins in the sperm entrapping gel, Semenogelin I and Semenogelin II, and fibronectin (Lilja, H. (1985). J. Clin. Invest. 76:1899; Lilja, H., Oldbring, J., Rannevik, G., et al. (1987). J. Clin. Invest. 80:281; McGee, R. S., Herr, J. C. (1988). Biol. Reprod. 39:499). The PSA mediated proteolysis of the gel-forming proteins generates several soluble Semenogelin I and Semenogelin II fragments and soluble fibronectin fragments with liquefaction of the ejaculate and release of progressively motile spermatoza (Lilja, H., Laurell, C. B. (1984). Scand. J. Clin. Lab. Invest. 44:447; McGee, R. S., Herr, J. C. (1987). Biol. Reprod. 37:431). Furthermore, PSA may proteolytically degrade IGFBP-3 (insulin-like growth factor binding protein 3) allowing IGF to stimulate specifically the growth of PSA secreting cells (Cohen et al., (1992) J. Clin. Endo. & Meta. 75:1046–1053).

PSA complexed to alpha 1-antichymotrypsin is the predominant molecular form of serum PSA and may account for up to 95% of the detected serum PSA (Christensson, A., Björk, T., Nilsson, O., et al. (1993). J. Urol. 150:100–105; Lilja, H., Christensson, A., Dahlén, U. (1991). Clin. Chem. 37:1618–1625; Stenman, U. H., Leinoven, J., Alfthan, H., et al. (1991). Cancer Res. 51:222–226). The prostatic tissue (normal, benign hyperplastic, or malignant tissue) is implicated to predominantly release the mature, enzymatically active form of PSA, as this form is required for complex formation with alpha 1-antichymotrypsin (Mast, A. E., Enghild, J. J., Pizzo, S. V., et al. (1991). Biochemistry 30:1723–1730; Perlmutter, D. H., Glover, G. I., Rivetna, M., et al. (1990). Proc. Natl. Acad. Sci. USA 87:3753–3757). Therefore, in the microenvironment of prostatic PSA secreting cells the PSA is believed to be processed and secreted in its mature enzymatically active form not complexed to any inhibitory molecule. PSA also forms stable complexes with alpha 2-macroglobulin, but as this results in encapsulation of PSA and complete loss of the PSA epitopes, the in vivo significance of this complex formation is unclear. A free, noncomplexed form of PSA constitutes a minor fraction of the serum PSA (Christensson, A., Björk, T., Nilsson, O., et al. (1993). J. Urol. 150:100–105; Lilja, H., Christensson, A., Dahlén, U. (1991). Clin. Chem. 37:1618–1625). The size of this form of serum PSA is similar to that of PSA in seminal fluid (Lilja, H., Christensson, A., Dahlén, U. (1991). Clin. Chem. 37:1618–1625) but it is yet unknown as to whether the free form of serum PSA may be a zymogen; an internally cleaved, inactive form of mature PSA; or PSA manifesting enzyme activity. However, it seems unlikely that the free form of serum PSA manifests enzyme activity, since there is considerable (100 to 1000 fold) molar excess of both unreacted alpha 1-antichymotrypsin and alpha 2-macroglobulin in serum as compared with the detected serum levels of the free 33 kDa form of PSA (Christensson, A., Björk, T., Nilsson, O., et al. (1993). J. Urol. 150:100–105; Lilja, H., Christensson, A., Dahlén, U. (1991). Clin. Chem. 37:1618–1625).

Serum measurements of PSA are useful for monitoring the treatment of adenocarcinoma of the prostate (Duffy, M. S. (1989). Ann. Clin. Biochem. 26:379–387; Brawer, M. K. and Lange, P. H. (1989). Urol. Suppl. 5:11–16; Hara, M. and Kimura, H. (1989). J. Lab. Clin. Med. 113:541–548), although above normal serum concentrations of PSA have also been reported in benign prostatic hyperplasia and subsequent to surgical trauma of the prostate (Lilja, H., Christensson, A., Dahlén, U. (1991). Clin. Chem. 37:1618–1625). Prostate metastases are also known to secrete immunologically reactive PSA since serum PSA is detectable at high levels in prostatectomized patients showing widespread metatstatic prostate cancer (Ford, T. F., Butcher, D. N., Masters, R. W., et al. (1985). Brit. J. Urology 57:50–55). Therefore, a cytotoxic compound that could be activated by the proteolytic activity of PSA should be prostate cell specific as well as specific for PSA secreting prostate metastases.

It is the object of this invention to provide a novel anti-cancer composition useful for the treatment of prostate cancer which comprises oligopeptides having solubility augmenting oligopeptide blocking groups in conjugation with a cytotoxic agent.

Another object of this invention is to provide a method of treating prostate cancer which comprises administration of the novel anti-cancer composition.

SUMMARY OF THE INVENTION

Chemical conjugates which comprise oligopeptides, having amino acid sequences that are selectively proteolytically cleaved by free prostate specific antigen (PSA), hydrophilic oligopeptide blocking groups and known cytotoxic agents are disclosed. Such conjugates are useful in the treatment of prostatic cancer and benign prostatic hypertrophy (BPH).

DETAILED DESCRIPTION OF THE INVENTION

The instant invention relates to novel anti-cancer compositions useful for the treatment of prostate cancer. Such compositions comprise the oligopeptides covalently bonded directly, or through a chemical linker, to a cytotoxic agent. The oligopeptides are chosen from oligomers that are selectively recognized by the free prostate specific antigen (PSA) and are capable of being proteolytically cleaved by the enzymatic activity of the free prostate specific antigen. Such a combination of an oligopeptide and cytotoxic agent may be termed a conjugate.

The conjugates of the instant invention are further characterized by having a hydrophilic blocking group at the N-terminus of the oligopeptide which contributes to the aqueous solubility of the conjugate. Examples of such hydrophilic blocking groups include but are not limited to hydroxylated and polyhydroxylated alkanoyl moieties and alkanoyl moieties that incorporate ether functionalities.

Ideally, the cytotoxic activity of the cytotoxic agent is greatly reduced or absent when the oligopeptide containing the PSA proteolytic cleavage site is bonded directly, or through a chemical linker, to the cytotoxic agent and is intact. Also ideally, the cytotoxic activity of the cytotoxic agent increases significantly or returns to the activity of the unmodified cytotoxic agent upon proteolytic cleavage of the attached oligopeptide at the cleavage site.

Furthermore, it is preferred that the oligopeptide is selected from oligopeptides that are not cleaved or are cleaved at a much slower rate in the presence of non-PSA proteolytic enzymes when compared to the cleavage of the oligopeptides in the presence of free enzymatically active PSA.

For the reasons above, it is desireable for the oligopeptide to comprise a short peptide sequence, preferably less than ten amino acids. Most preferably the oligopeptide comprises seven or fewer amino acids. Because the conjugate preferably comprises a short amino acid sequence, the solubility of the conjugate may be influenced to a greater extent by the generally hydrophobic character of the cytotoxic agent component. Therefore, the hydrophilic blocking groups of the instant conjugates are selected to offset or diminish such a hydrophobic contribution by the cytotoxic agent.

While it is not necessary for practicing this aspect of the invention, a preferred embodiment of this invention is a conjugate wherein the oligopeptide, and the chemical linker if present, are detached from the cytotoxic agent by the proteolytic activity of the free PSA and any other native proteolytic enzymes present in the tissue proximity, thereby releasing unmodified cytotoxic agent into the physiological environment at the place of proteolytic cleavage. Pharmaceutically acceptable salts of the conjugates are also included.

It is understood that the oligopeptide that is conjugated to the cytotoxic agent, whether through a direct covalent bond or through a chemical linker, does not need to be the oligopeptide that has the greatest recognition by free PSA and is most readily proteolytically cleaved by free PSA. Thus, the oligopeptide that is selected for incorporation in such an anti-cancer composition will be chosen both for its selective, proteolytic cleavage by free PSA and for the cytotoxic activity of the cytotoxic agent-proteolytic residue conjugate (or, in what is felt to be an ideal situation, the unmodified cytotoxic agent) which results from such a cleavage. The term "selective" as used in connection with the proteolytic PSA cleavage means a greater rate of cleavage of an oligopeptide component of the instant invention by free PSA relative to cleavage of an oligopeptide which comprises a random sequence of amino acids. Therefore, oligopeptide component of the instant invention is a prefered substrate of free PSA. The term "selective" also indicates that the oligopeptide is proteolytically cleaved by free PSA between two specific amino acids in the oligopeptide.

The oligopeptide components of the instant invention are selectively recognized by the free prostate specific antigen (PSA) and are capable of being proteolytically cleaved by the enzymatic activity of the free prostate specific antigen. Such oligopeptides comprise an oligomer selected from:

a) AsnLysIleSerTyrGln|Ser (SEQ.ID.NO.: 1),
b) LysIleSerTyrGln|Ser (SEQ.ID.NO.: 2),
c) AsnLysIleSerTyrTyr|Ser (SEQ.ID.NO.: 3),
d) AsnLysAlaSerTyrGln|Ser (SEQ.ID.NO.: 4),
e) SerTyrGln|SerSer (SEQ.ID.NO.: 5);
f) LysTyrGln|SerSer (SEQ.ID.NO.: 6);
g) hArgTyrGln|SerSer (SEQ.ID.NO.: 7);
h) hArgChaGln|SerSer (SEQ.ID.NO.: 8);
i) TyrGln|SerSer (SEQ.ID.NO.: 9);
j) TyrGln|SerLeu (SEQ.ID.NO.: 10);
k) TyrGln|SerNle (SEQ.ID.NO.: 11);
l) ChgGln|SerLeu (SEQ.ID.NO.: 12);
m) ChgGln|SerNle (SEQ.ID.NO.: 13);

wherein hArg is homoarginine, Cha is cyclohexylalanine and Chg is cyclohexylglycine.

In an embodiment of the instant invention, the oligopeptide comprises an oligomer that is selected from:

a) AsnLysIleSerTyrGln|SerSer (SEQ.ID.NO.: 14),
b) AsnLysIleSerTyrGln|SerAla (SEQ.ID.NO.: 15),
c) AlaAsnLysIleSerTyrTyr|Ser (SEQ.ID.NO.: 16),
d) AlaAsnLysAlaSerTyrGln|Ser (SEQ.ID.NO.: 17),
e) SerTyrGln|SerSerThr (SEQ.ID.NO.: 18),
f) SerTyrGln|SerSerSer (SEQ.ID.NO.: 19),
g) LysTyrGln|SerSerSer (SEQ.ID.NO.: 20),
h) hArgTyrGln|SerSerSer (SEQ.ID.NO.: 21),
i) SerTyrGln|SerSerLeu (SEQ.ID.NO.: 22);
j) SerTyrGln|SerLeu (SEQ.ID.NO.: 23);
k) SerChgGln|SerLeu (SEQ.ID.NO.: 24);
l) hArgChgGln|SerLeu (SEQ.ID.NO.: 25); and
m) hArgTyrGln|SerLeu (SEQ.ID.NO.: 26).

In a more preferred embodiment of the instant invention, the oligopeptide comprises an oligomer selected from:

GlyGluAsnGlyValGlnLysAspValSerGlnArgSerIleTyr|SerGlnThrGlu (SEQ.ID.NO.: 27),
AlaSerTyrGln|SerSerLeu (SEQ.ID.NO.: 28);
SerhArgChgGln|SerLeu (SEQ.ID.NO.: 29);
hArgSerSerTyrGln|SerNle (SEQ.ID.NO.: 30);
hArgAlaSerChgGln|SerLeu (SEQ.ID.NO.: 31);
hArgSerSerTyrGln|SerLeu (SEQ.ID.NO.: 32);
hArgSerSerChg|SerLeu (SEQ.ID.NO.: 33);
SerhArgChgGln|SerLeu (SEQ.ID.NO.: 34);
hArgTyrGln|SerLeu (SEQ.ID.NO.: 35);
hArgSerSerChgGln|SerLeu (SEQ.ID.NO.: 36);
SerhArgTyrGln|SerLeu (SEQ.ID.NO.: 37);
SerSerTyrGln|SerLeu (SEQ.ID.NO.: 38);
SerSerSerChgGln|SerLeu (SEQ.ID.NO.: 39);
3PAL-SerSerChgGln|SerLeu (SEQ.ID.NO.: 40);
SerSerChgGln|SerLeu (SEQ.ID.NO.: 41);
SerSerSerChgGln|Ser(dLeu) (SEQ.ID.NO.: 42);
SerSerSerChgGln|SerVal (SEQ.ID.NO.: 43);
ProSerSerChgGln|SerVal (SEQ.ID.NO.: 44);
GlySerSerChgGln|SerLeu (SEQ.ID.NO.: 45);
hSerSerSerChgGln|SerLeu (SEQ.ID.NO.: 46);
hArgSerSerChgGln|SerNle (SEQ.ID.NO.: 47);
hArgTyrGln|SerSerSerLeu (SEQ.ID.NO.: 55);
LysTyrGln|SerSerSerLeu (SEQ.ID.NO.: 56);
SerTyrGln|SerSerSerLeu (SEQ.ID.NO.: 57);
SerSerChgGln-Ser(dLeu) (SEQ.ID.NO.: 58); and
3PAL-SerSerChgGln-Ser(dLeu) (SEQ.ID.NO.: 59); and
AlaSerChgGln-SerLeu (SEQ.ID.NO.: 60).

The phrase "oligomers that comprise an amino acid sequence" as used hereinabove, and elsewhere in the Detailed Description of the Invention, describes oligomers of from about 3 to about 100 amino acids residues which include in their amino acid sequence the specific amino acid sequence decribed and which are therefore proteolytically cleaved within the amino acid sequence described by free PSA. Preferably, the oligomer is from 5 to 10 amino acid residues. Thus, for example, the following oligomer: hArgSerAlaChgGln|SerLeu (SEQ.ID.NO.: 48); comprises the amino acid sequence: ChgGln|SerLeu (SEQ.ID.NO.: 12); and would therefore come within the instant invention. It is understood that such oligomers do not include semenogelin I and semenogelin II.

A person of ordinary skill in the peptide chemistry art would readily appreciate that certain amino acids in a biologically active oligopeptide may be replaced by other homologous, isosteric and/or isoelectronic amino acids wherein the biological activity of the original oligopeptide has been conserved in the modified oligopeptide. Certain unnatural and modified natural amino acids may also be utilized to replace the corresponding natural amino acid in the oligopeptides of the instant invention. Thus, for example, tyrosine may be replaced by 3-iodotyrosine, 2-methyltyrosine, 3-fluorotyrosine, 3-methyltyrosine and the like. Further for example, lysine may be replaced with N'-(2-imidazolyl)lysine and the like. The following list of amino acid replacements is meant to be illustrative and is not limiting:

| Original Amino Acid | Replacement Amino Acid(s) |
|---|---|
| Ala | Gly |
| Arg | Lys, Ornithine |
| Asn | Gln |
| Asp | Glu |
| Glu | Asp |
| Gln | Asn |
| Gly | Ala |
| Ile | Val, Leu, Met, Nle |
| Leu | Ile, Val, Met, Nle |
| Lys | Arg, Ornithine |
| Met | Leu, Ile, Nle, Val |
| Ornithine | Lys, Arg |
| Phe | Tyr, Trp |
| Ser | Thr |
| Thr | Ser |
| Trp | Phe, Tyr |
| Tyr | Phe, Trp |
| Val | Leu, Ile, Met, Nle |

Thus, for example, the following oligopeptides may be synthesized by techniques well known to persons of ordinary skill in the art and would be expected to be proteolytically cleaved by free PSA:
AsnArgIleSerTyrGln|Ser (SEQ.ID.NO.: 49)
AsnLysValSerTyrGln|Ser (SEQ.ID.NO.: 50)
AsnLysMetSerTyrGln|SerSer (SEQ.ID.NO.: 51)
AsnLysLeuSerTyrGln|SerSer (SEQ.ID.NO.: 52)
AsnLysIleSerTyrGln|Ser (SEQ.ID.NO.: 53)
GlnLysIleSerTyrGln|SerSer (SEQ.ID.NO.: 54).

The inclusion of the symbol "|" within an amino acid sequence indicates the point within that sequence where the oligopeptide is proteolytically cleaved by free PSA.

The compounds of the present invention may have asymmetric centers and occur as racemates, racemic mixtures, and as individual diastereomers, with all possible isomers, including optical isomers, being included in the present invention. Unless otherwise specified, named amino acids are understood to have the natural "L" stereoconfiguration.

The following abbreviations are utilized in the specification and figures to denote the indicated amino acids and moieties:

hR or hArg: homoarginine
hY or hTyr: homotyrosine
Cha: cyclohexylalanine
Amf: 4-aminomethylphenylalanine
DPL: 2-(4,6-dimethylpyrimidinyl)lysine
(imidazolyl)K: N'-(2-imidazolyl)lysine
$Me_2PO_3$—Y: O-dimethylphosphotyrosine
O—Me—Y: O-methyltyrosine
TIC: tetrahydro-3-isoquinoline carboxylic acid
DAP: 1,3-diaminopropane
TFA: trifluoroacetic acid
AA: acetic acid
3PAL 3-pyridyl-alanine The conjugates of the instant invention comprise oligomers wherein the N-terminus amino acid is modified with a hydrophilic blocking group. Such blocking groups are chosen based upon the presence of hydrophilic functionality. The presence of the hydrophilic functionality distinquishes the instant conjugates from conjugates previously disclosed that also had N-terminus blocking groups. Such blocking of the terminal amino group may also reduce or eliminate the enzymatic degradation of such peptidyl therapeutic agents by the action of exogenous amino peptidases which are present in the blood plasma of warm blooded animals. Blocking groups that increase the hydrophilicity of the conjugates and therefore increase the aqueous solubility of the conjugates include but are not limited to hydroylated alkanoyl, polyhydroxylated alkanoyl, polyethylene glycol, glycosylates, sugars and crown ethers.

Preferably the blocking group is selected from

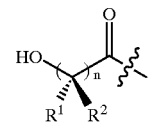
(a)

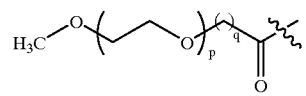
(b)

wherein:
$R^1$ and $R^2$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^3C(O)NR^3$—, $(R^3)_2NC(O)$—, $R^3{}_2N$—C$(NR^3)$—, $R^4S(O)_mNH$, CN, $NO_2$, $R^3C(O)$—, $N_3$, —N$(R^3)_2$, or $R^4OC(O)NR^3$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^3O$—, $R^4S(O)_mNH$, $R^3C(O)NR^3$—, $(R^3)_2NC(O)$—, $R^3{}_2N$—C$(NR^3)$—, CN, $R^3C(O)$—, $N_3$, —N$(R^3)_2$, and $R^4OC(O)$—NR$^3$—; or $R^1$ and $R^2$ are combined to form —$(CH_2)_s$— wherein one of the carbon atoms is optionally replaced by a moiety selected from: O, $S(O)_m$, —NC(O)—, NH and —N(COR$^4$)—;

R$^3$ is selected from: hydrogen, aryl, substituted aryl, heterocycle, substituted heterocycle, C$_1$–C$_6$ alkyl and C$_3$–C$_{10}$ cycloalkyl;

R$^4$ is selected from: aryl, substituted aryl, heterocycle, substituted heterocycle, C$_1$–C$_6$ alkyl and C$_3$–C$_{10}$ cycloalkyl;

m is 0, 1 or 2;

n is 1, 2, 3 or 4;

p is zero or an integer between 1 and 100; and q is 0 or 1, provided that if p is zero, q is 1; and s is 3, 4 or 5.

The conjugates of the present invention may have asymmetric centers and occur as racemates, racemic mixtures, and as individual diastereomers, with all possible isomers, including optical isomers, being included in the present invention. When any variable (e.g. aryl, heterocycle, R$^3$ etc.) occurs more than one time in any constituent, its definition on each occurence is independent of every other occurence. For example, HO(CR$^1$R$^2$)$_2$— represents HOCH$_2$CH$_2$—, HOCH$_2$CH(OH)—, HOCH(CH$_3$)CH(OH)—, etc. Also, combinations of substituents and/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aralkyl and aroyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein in the terms "substituted C$_{1-8}$ alkyl", "substituted aryl" and "substituted heterocycle" include moieties containing from 1 to 3 substituents in addition to the point of attachment to the rest of the compound. Such additional substituents are selected from F, Cl, Br, CF$_3$, NH$_2$, N(C$_1$–C$_6$ alkyl)$_2$, NO$_2$, CN, (C$_1$–C$_6$ alkyl)O—, —OH, (C$_1$–C$_6$ alkyl)S(O)$_m$—, (C$_1$–C$_6$ alkyl)C(O)NH—, H$_2$N—C(NH)—, (C$_1$–C$_6$ alkyl)C(O)—, (C$_1$–C$_6$ alkyl)OC(O)—, N$_3$, (C$_1$–C$_6$ alkyl)OC(O)NH— and C$_1$–C$_{20}$ alkyl.

When R$^1$ and R$^2$ are combined to form —(CH$_2$)$_s$—, the cyclic moieties and heteroatom-containing cyclic moieties so defined include, but are not limited to:

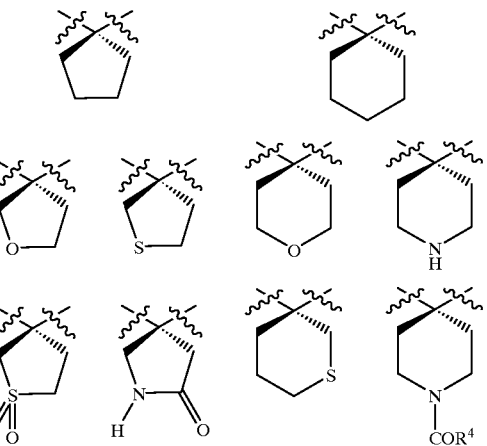

As used herein, the term "PEG" represents certain polyethylene glycol containing substituents having the designated number of ethyleneoxy subunits. Thus the term PEG (2) represents

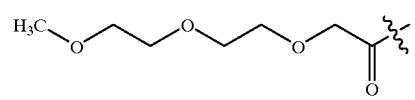

and the term PEG(6) represents

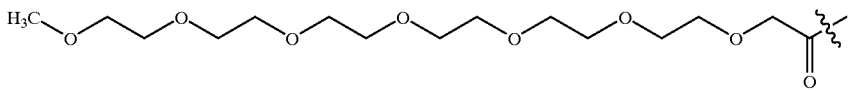

As used herein, the term "(d)(2,3-dihydroxypropionyl)" represents the following structure:

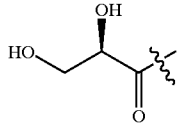

As used herein, the term "(2R,3S) 2,3,4-trihydroxybutanoyl" represents the following structure:

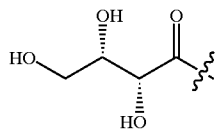

Because the conjugates of the invention can be used for modifying a given biological response, cytotoxic agent is not to be construed as limited to classical chemical therapeutic agents. For example, the cytotoxic agent may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

The preferred cytotoxic agents include, in general, alkylating agents, antiproliferative agents, tubulin binding agents and the like. Preferred classes of cytotoxic agents include, for example, the anthracycline family of drugs, the vinca drugs, the mitomycins, the bleomycins, the cytotoxic nucleosides, the taxanes, the pteridine family of drugs, diynenes and the podophyllotoxins. Particularly useful members of those classes include, for example, doxorubicin, carminomycin, daunorubicin, aminopterin, methotrexate, methopterin, dichloro-methotrexate, mitomycin C, porfiromycin, 5-fluorouracil, 6-mercaptopurine, cytosine arabinoside, podophyllotoxin, or podophyllotoxin derivatives such as etoposide or etoposide phosphate, melphalan, vinblastine, vincristine, leurosidine, vindesine, leurosine, taxol and the like. Other useful cytotoxic agents include estramustine, cisplatin and cyclophosphamide. One skilled in the art may make chemical modifications to the desired cytotoxic agent in order to make reactions of that compound more convenient for purposes of preparing conjugates of the invention.

A highly preferred group of cytotoxic agents for the present invention include drugs of the following formulae:

The Methotrexate Group of Formula (1)

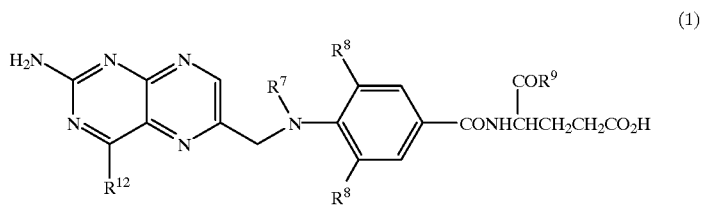

in which $R^{12}$ is amino or hydroxy;

$R^7$ is hydrogen or methyl;

$R^8$ is hydrogen, fluoro, chloro, bromo or iodo;

$R^9$ is hydroxy or a moiety which completes a salt of the carboxylic acid;

The Mitomycin Group of Formula (2)

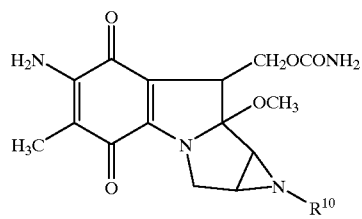

in which $R^{10}$ is hydrogen or methyl;

The Bleomycin Group of Formula (3)
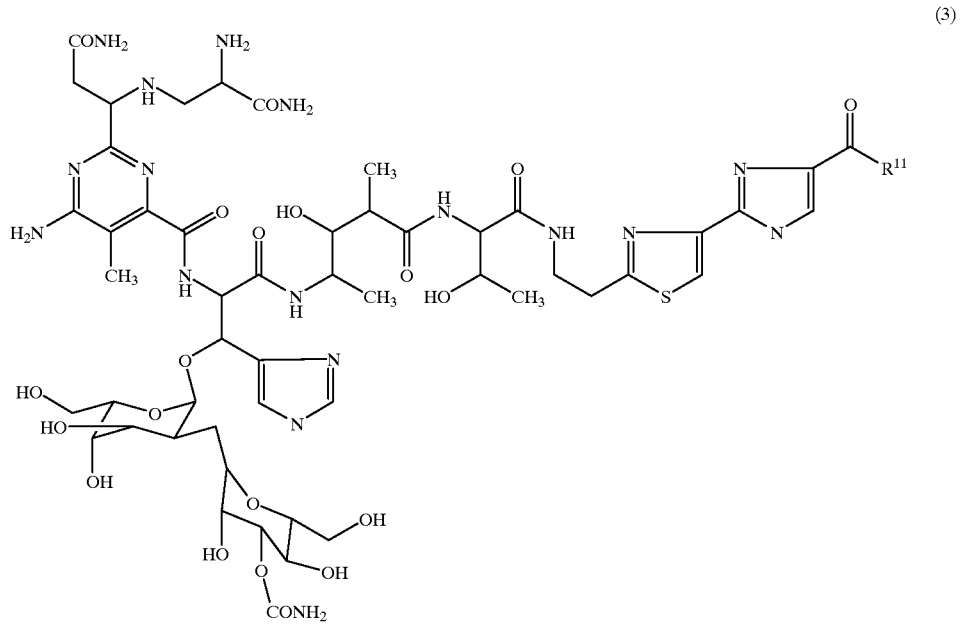
in which $R^{11}$ is hydroxy, amino, $C_1$–$C_3$ alkylamino, di($C_1$–$C_3$ alkyl)amino, $C_4$–$C_6$ polymethylene amino,
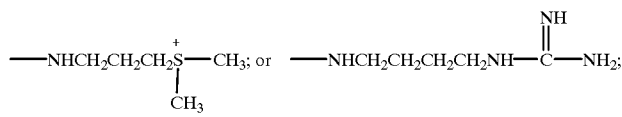
Melphalan of Formula (4)
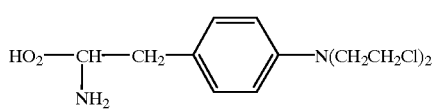
6-Mercaptopurine of Formula (5)
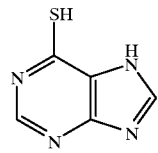
A Cytosine Arabinoside of Formula (6)
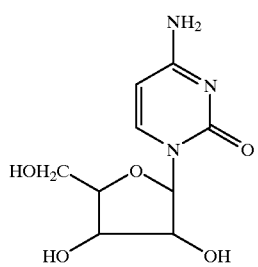

The Podophyllotoxins of Formula (7)

(7)

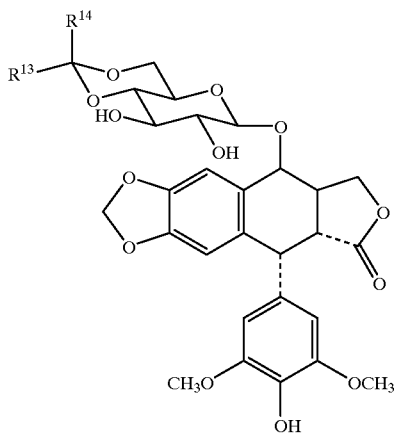

in which
R$^{13}$ is hydrogen or methyl;
R$^{14}$ is methyl or thienyl;
or a phosphate salt thereof;

The Vinca Alkaloid Group of Drugs of Formula (8)

(8)

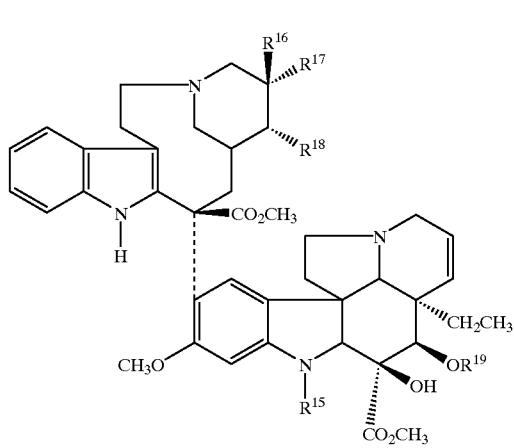

in which
R$^{15}$ is H, CH$_3$ or CHO; when R$^{17}$ and R$^{18}$ are taken singly;
R$^{18}$ is H, and one of R$^{16}$ and R$^{17}$ is ethyl and the other is H or OH; when R$^{17}$ and R$^{18}$ are taken together with the carbons to which they are attached, they form an oxirane ring in which case R$^{16}$ is ethyl;
R$^{19}$ is hydrogen, (C$_1$–C$_3$ alkyl)-CO, or chlorosubstituted (C$_1$–C$_3$ alkyl)-CO;

Difluoronucleosides of Formula (9)

(9)

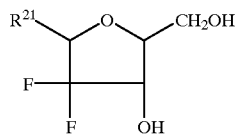

in which

R$^{21}$ is a base of one of the formulae:

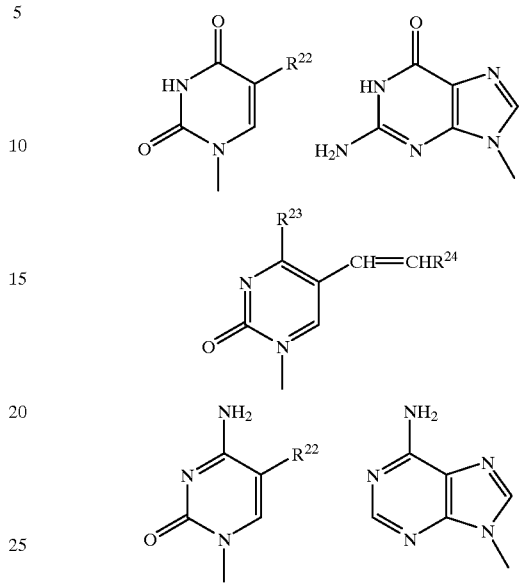

in which

R$^{22}$ is hydrogen, methyl, bromo, fluoro, chloro or iodo;
R$^{23}$ is —OH or —NH$_2$;
R$^{24}$ is hydrogen, bromo, chloro or iodo; or, The Anthracyclines Antibiotics of Formula (10)

(10)

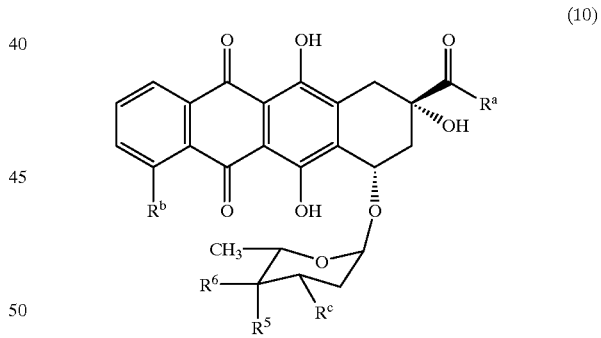

wherein

R$^a$ is —CH$_3$, —CH$_2$OH, —CH$_2$OCO(CH$_2$)$_3$CH$_3$, or —CH$_2$OCOCH(OC$_2$H$_5$)$_2$;

R$^b$ is —OCH$_3$, —OH or —H;

R$^c$ is —NH$_2$, —NHCOCF$_3$, 4-morpholinyl, 3-cyano-4-morpholinyl, 1-piperidinyl, 4-methoxy-1-piperidinyl, benzylamine, dibenzylamine, cyanomethylamine, or 1-cyano-2-methoxyethyl amine;

R$^5$ is —OH —OTHP or —H; and

R$^6$ is —OH or —H provided that R$^6$ is not —OH when R$^5$ is —OH or —OTHP.

Estramustine (11)

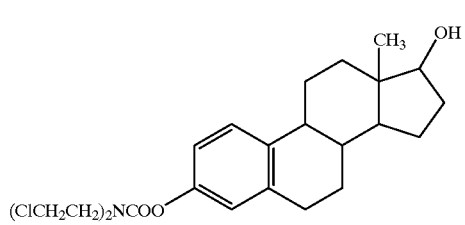

Cyclophosphamide (12)

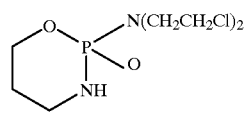

The most highly preferred drugs are the anthracycline antiobiotic agents of Formula (10), described previously. One skilled in the art understands that this structural formula includes compounds which are drugs, or are derivatives of drugs, which have acquired in the art different generic or trivial names. Table 1, which follows, represents a number of anthracycline drugs and their generic or trivial names and which are especially preferred for use in the present invention.

TABLE 1

| Compound | $R^a$ | $R^b$ | $R^c$ | $R_5$ | $R_6$ |
|---|---|---|---|---|---|
| daunorubicin[a] | $CH_3$ | $OCH_3$ | $NH_2$ | OH | H |
| doxorubicin[b] | $CH_2OH$ | $OCH_3$ | $NH_2$ | OH | H |
| detorubicin | $CH_2OCOCH(OC_2H_5)_2$ | $OCH_3$ | $NH_2$ | OH | H |
| carminomycin | $CH_3$ | OH | $NH_2$ | OH | H |
| idarubicin | $CH_3$ | H | $NH_2$ | OH | H |
| epirubicin | $CH_2OH$ | $OCH_3$ | $NH_2$ | OH | OH |
| esorubicin | $CH_2OH$ | $OCH_3$ | $NH_2$ | H | H |
| THP | $CH_2OH$ | $OCH_3$ | $NH_2$ | OTHP | H |
| AD-32 | $CH_2OCO(CH_2)_3CH_3$ | $OCH_3$ | $NHCOCF_3$ | OH | H |

[a]"daunomycin" is an alternative name for daunorubicin
[b]"adriamycin" is an alternative name for doxorubicin Of the compounds shown in Table 1, the most highly preferred cytotoxic agents are doxorubicin, vinblastine and desacetyl-vinblastine. Doxorubicin (also referred to herein as "DOX") is that anthracycline of Formula (10) in which $R^a$ is —$CH_2OH$, $R^c$ is —$OCH_3$, $R^4$ is —$NH_2$, $R^5$ is —OH, and $R^6$ is —H.

The blocked oligopeptide-cytotoxic agent conjugate of the instant invention wherein the cytotoxic agent is the preferred cytotoxic agent doxorubicin may be described by the general formula I below:

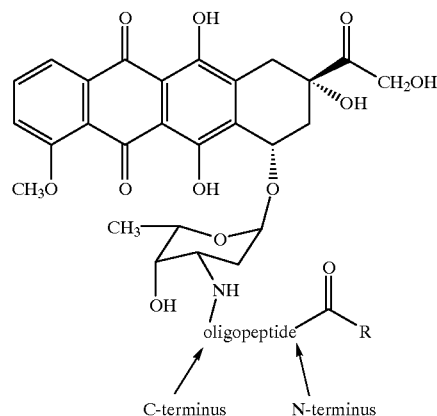

wherein:

oligopeptide is an oligopeptide which is selectively recognized by the free prostate specific antigen (PSA) and is capable of being proteolytically cleaved by the enzymatic activity of the free prostate specific antigen, and wherein the C-terminus carbonyl is covalently bound to the amine of doxorubicin and the N-terminus amine is covalently bound to the carbonyl of the blocking group;

R is selected from

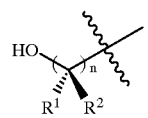

(a)

-continued (b)
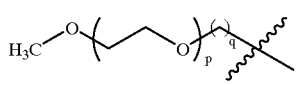

R¹ and R² are independently selected from: hydrogen, OH, $C_1$–$C_6$ alkyl, $C_1$–$C_6$ alkoxy, $C_1$–$C_6$ aralkyl and aryl;
n is 1, 2, 3 or 4;
p is zero or an integer between 1 and 100;
q is 0 or 1, provided that if p is zero, q is 1;
or the pharmaceutically acceptable salt thereof.

In a preferred embodiment of the oligopeptide-cytotoxic agent conjugate:

R is selected from

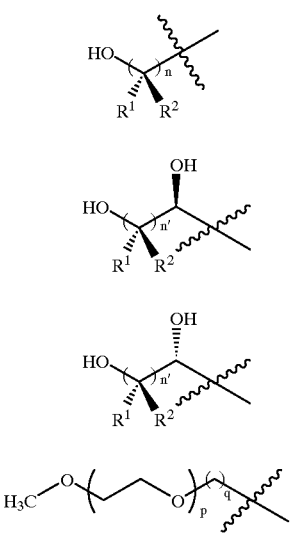

(a)

(b)

(c)

(b)

R¹ and R² are independently selected from: hydrogen, $C_1$–$C_6$ alkyl and aryl;
n is 1, 2, 3 or 4;
n' is 0, 1, 2 or 3;
p is zero or an integer between 1 and 14;
q is 0 or 1, provided that if p is zero, q is 1;
or the pharmaceutically acceptable salt thereof.

The following compounds are specific examples of the oligopeptide-cytotoxic agent conjugate of the instant invention:

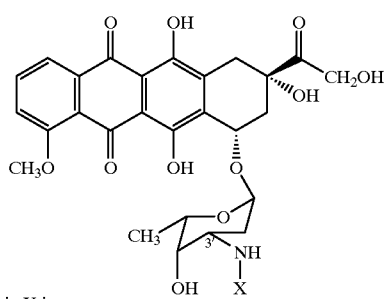

wherein X is:

(SEQ.ID.NO.: 61)

(SEQ.ID.NO.: 62)

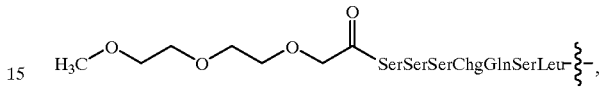
(SEQ.ID.NO.: 63)

or the pharmaceutically acceptable salt thereof.

Further examples of conjugates of an oligopeptide and doxorubicin wherein the N-terminus of the oligopeptide is blocked by a hydrophilic moiety and the C-terminus of the oligopeptide is attached to the doxorubicin at the 3'-amine are as follows:

2-hydroxyacetyl-hArgSerSerTyrGln-SerNle-DOX (3') (SEQ.ID.NO.: 64)
2-hydroxyacetyl-hArgSerSerChgGln-SerNle-DOX (3') (SEQ.ID.NO.: 65)
2-hydroxyacetyl-SerhArgChgGln-SerLeu-DOX (3') (SEQ.ID.NO.: 66)
2-hydroxyacetyl-hArgSerSerChgGln-SerLeu-DOX (3') (SEQ.ID.NO.: 67)
2-hydroxyacetyl-hArgAlaSerChgGln-SerLeu-DOX (3') (SEQ.ID.NO.: 68)
(d) 2,3-dihydroxypropionyl-SerhArgChgGln-SerLeu-DOX (3') (SEQ.ID.NO.: 69)
(l) 2,3-dihydroxypropionyl-SerhArgChgGln-SerLeu-DOX (3') (SEQ.ID.NO.: 70)
PEG(2)-SerhArgChgGln-SerLeu-DOX (3') (SEQ.ID.NO.: 71)
PEG(2)-hArgChgGln-SerLeu-DOX (3') (SEQ.ID.NO.: 72)
(2R,3S) 2,3,4-trihydroxybutanoyl-hArgChgGln-SerLeu-DOX (3') (SEQ.ID.NO.: 73)
PEG(2)-SerhArgTyrGln-SerLeu-DOX(3') (SEQ.ID.NO.: 74)
PEG(2)-hArgTyrGln-SerSerSerLeu-DOX (3') (SEQ.ID.NO.: 75)
PEG(2)-LysTyrGln-SerSerSerLeu-DOX (3') (SEQ.ID.NO.: 76)
2-hydroxyacetyl-hArgSerSerTyrGln-SerLeu-DOX (3') (SEQ.ID.NO.: 77)
(l)(2,3-dihydroxypropionyl)hArgSerSerChgGlnSerLeu-DOX (3') (SEQ.ID.NO.: 78)
PEG(2)-hArgSerSerChgGln-SerLeu-DOX (3') (SEQ.ID.NO.: 79)
2-hydroxyacetyl-SerTyrGln-SerSerSerLeu-DOX (3') (SEQ.ID.NO.: 80)
PEG(16)-SerhArgTyrGln-SerLeu-DOX (3') (SEQ.ID.NO.: 81)
(2R,3S) 2,3,4-trihydroxybutanoyl-SerhArgChgGln-SerLeu-DOX (3') (SEQ.ID.NO.: 82)
PEG(2)-SerhArgTyrGln-SerLeu-DOX (3') (SEQ.ID.NO.: 83)
(d)(2,3-dihydroxypropionyl)-hArgSerSerChgGln-SerLeu-DOX(3') (SEQ.ID.NO.: 84)
(l)(2,3-dihydroxypropionyl)SerSerSerChgGln-Ser(dLeu)-DOX (3') (SEQ.ID.NO.: 85)
(d)(2,3-dihydroxypropionyl)SerSerSerChgGln-SerLeu-DOX (3') (SEQ.ID.NO.: 86)

(l)(2,3-dihydroxypropionyl)SerSerSerChgGln-SerLeu-DOX (3') (SEQ.ID.NO.: 87)

(l)(2,3-dihydroxypropionyl)SerSerChgGln-Ser(dLeu)-DOX (3') (SEQ.ID.NO.: 88)

(d)(2,3-dihydroxypropionyl)SerSerChgGln-SerLeu-DOX (3') (SEQ.ID.NO.: 89)

PEG(2)-SerSerChgGln-Ser(dLeu)-DOX (3') (SEQ.ID.NO.: 90)

PEG(2)SerSerChgGln-SerLeu-DOX (3') (SEQ.ID.NO.: 91)

PEG(2)-SerSerSerChgGln-Ser(dLeu)-DOX (3') (SEQ.ID.NO.: 92)

(2,3-dihydroxypropionyl)-3PAL-SerSerChgGln-Ser(dLeu)-DOX (3') (SEQ.ID.NO.: 93)

(d)(2,3-dihydroxypropionyl)-3PAL-SerSerChgGln-SerLeu-DOX (3') (SEQ.ID.NO.: 94)

(l)(2,3-dihydroxypropionyl)-SerSerChgGln-SerLeu-DOX (3') (SEQ.ID.NO.: 95)

(2,3-dihydroxypropionyl)-hSerSerSerChgGln-SerLeu-DOX (3') (SEQ.ID.NO.: 96)

PEG(2)-AlaSerChgGln-SerLeu-DOX (3') (SEQ.ID.NO.: 97)

PEG(6)-SerSerChgGln-SerLeu-DOX (3') (SEQ.ID.NO.: 98)

PEG(6)-SerSerSerChgGln-SerLeu-DOX (3') (SEQ.ID.NO.: 99)

PEG(6)-AlaSerChgGln-SerLeu-DOX (3') (SEQ.ID.NO.: 100)

PEG(4)-3PALSerSerChgGln-SerLeu-DOX (3') (SEQ.ID.NO.: 101)

or the pharmaceutically acceptable salt thereof.

The oligopeptide-cytotoxic agent conjugate of the instant invention wherein the cytotoxic agent is the preferred cytotoxic agent vinblastine or desacetylvinblastine may be described by the general formula II below:

II

[Structure of formula II with $X_L$-oligopeptide-R substituent]

wherein:

oligopeptide is an oligopeptide which is specifically recognized by the free prostate specific antigen (PSA) and is capable of being proteolytically cleaved by the enzymatic activity of the free prostate specific antigen;

$X_L$ is $-NH-(CH_2)_r-NH-$

R is selected from (a)

[Structure (a) with HO, $R^1$, $R^2$, n]

(b)

[Structure (b) with $H_3C-O$, p, q]

$R^1$ and $R^2$ are independently selected from: hydrogen, OH, $C_1-C_6$ alkyl, $C_1-C_6$ alkoxy, $C_1-C_6$ aralkyl and aryl;

$R^{19}$ is hydrogen, ($C_1-C_3$ alkyl)-CO, or chlorosubstituted ($C_1-C_3$ alkyl)-CO;

n is 1, 2, 3 or 4;

p is zero or an integer between 1 and 100;

q is 0 or 1, provided that if p is zero, q is 1;

r is 1, 2, 3, 4 or 5, or the pharmaceutically acceptable salt thereof.

The another embodiment of the oligopeptide-cytotoxic agent conjugate of the instant invention wherein the cytotoxic agent is the preferred cytotoxic agent vinblastine or desacetylvinblastine may be described by the general formula III below:

III

[Structure of formula III with CO-oligopeptide-$NR^dR^e$ substituent, indicating N-terminus and C-terminus]

wherein:

oligopeptide is an oligopeptide which is specifically recognized by the free prostate specific antigen (PSA) and is capable of being proteolytically cleaved by the enzymatic activity of the free prostate specific antigen, $R^d$ and $R^e$ are independently selected from: hydrogen, $C_1-C_6$-alkyl, $-C_1-C_6$-alkyl-OH, $-C_1-C_6$-alkyl-di-OH, $-C_1-C_6$-alkyl-tri-OH and

[Structure with $H_3C-O$, p, q]

provided that at least one $R^d$ and $R^e$ are not hydrogen or $C_1-C_6$-alkyl, or $R^d$ and $R^e$ are combined to form a $-CH_2CH_2OCH_2CH_2-$ diradical;

$R^{19}$ is hydrogen, $(C_1-C_3$ alkyl)-CO, or chlorosubstituted $(C_1-C_3$ alkyl)-CO;

p is zero or an integer between 1 and 100;

q is 0 or 1, provided that if p is zero, q is 1;

The following compounds are specific examples of the oligopeptide-desacetylvinblastine conjugate of the instant invention:

(SEQ.ID.NO.:61)

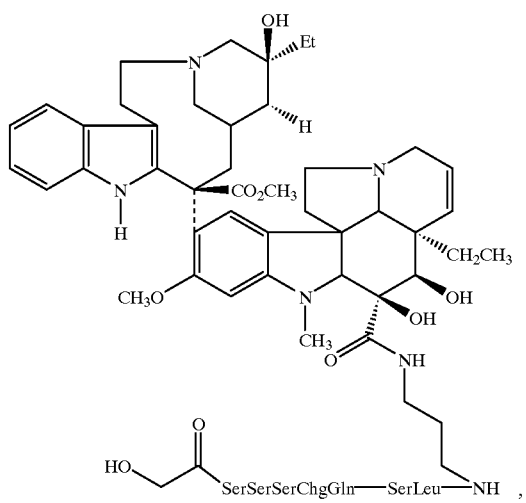

(SEQ.ID.NO.:102)

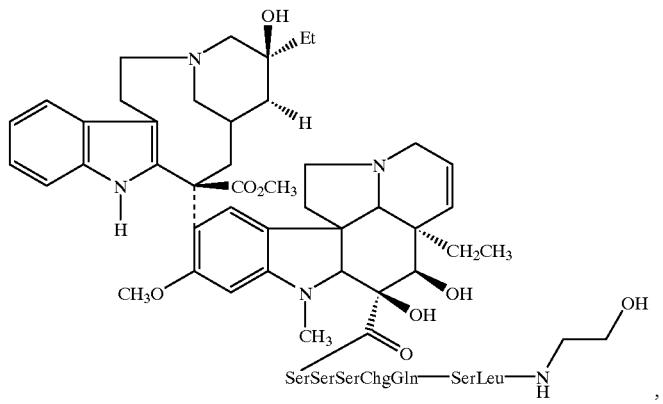

or the pharmaceutically acceptable salt thereof.

The oligopeptides, peptide subunits and peptide derivatives (also termed "peptides") of the present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965; Bodansky et al., "Peptide Synthesis", Interscience Publishers, 1966; McOmie (ed.) "Protective Groups in Organic Chemistry", Plenum Press, 1973; Barany et al., "The Peptides: Analysis, Synthesis, Biology" 2, Chapter 1, Academic Press, 1990, and Stewart et al., "Solid Phase Peptide Synthesis", Second Edition, Pierce Chemical Company, 1984. The teachings of these works are hereby incorporated by reference.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenyl-acetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The conjugates of the instant invention which comprise the oligopeptide containing the PSA cleavage site and a cytotoxic agent may similarly be synthesized by techniques well known in the medicinal chemistry art. For example, a free amine moiety on the cytotoxic agent may be covalently attached to the oligopeptide at the carboxyl terminus such that an amide bond is formed. Similarly, an amide bond may be formed by covalently coupling an amine moiety of the oligopeptide and a carboxyl moiety of the cytotoxic agent. For these purposes a reagent such as 2-(1H-benzotriazol-1-yl)-1,3,3-tetramethyluronium hexafluoro-phosphate known as HBTU) and 1-hyroxybenzotriazole hydrate (known as HOBT), dicyclohexyl-carbodiimide (DCC), N-ethyl-N-(3-dimethylaminopropyl)-carbodiimide (EDC), diphenylphosphorylazide (DPPA), benzotriazol-1-yl-oxy-tris-(dimethylamino)phosphonium hexafluoro-phosphate (BOP) and the like, used in combination or singularly, may be utilized.

Furthermore, the instant conjugate may be formed by a non-peptidyl bond between the PSA cleavage site and a cytotoxic agent. For example, the cytotoxic agent may be covalently attached to the carboxyl terminus of the oligopeptide via a hydroxyl moiety on the cytotoxic agent, thereby forming an ester linkage. For this purpose a reagent such as a combination of HBTU and HOBT, a combination of BOP and imidazole, a combination of DCC and DMAP, and the like may be utilized. The carboxylic acid may also be activated by forming the nitro-phenyl ester or the like and reacted in the presence of DBU (1,8-diazabicyclo[5,4,0]undec-7-ene.

The instant conjugate may also be formed by attachment of the oligopeptide to the cytotoxic agent via a linker unit. Such linker units include, for example, a biscarbonyl alkyl diradical whereby an amine moiety on the cytotoxic agent is connected with the linker unit to form an amide bond and the amino terminus of the oligopeptide is connected with the other end of the linker unit also forming an amide bond. Conversely, a diaminoalkyl diradical linker unit, whereby a carbonyl moiety on the cyctotoxic agent is covalently attacted to one of the amines of the linker unit while the other amine of the linker unit is covalently attached to the C terminus of the oligopeptide, may also be useful. Other such linker units which are stable to the physiological environment when not in the presence of free PSA, but are cleavable upon the cleavage of the PSA proteolytic cleavage site, are also envisioned. Furthermore, linker units may be utilized that, upon cleavage of the PSA proteolytic cleavage site, remain attached to the cytotoxic agent but do not significantly decrease the cytotoxic activity of such a post-cleavage cytotoxic agent derivative when compared with an unmodified cytotoxic agent.

One skilled in the art understands that in the synthesis of compounds of the invention, one may need to protect various reactive functionalities on the starting compounds and intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to *Protective Groups in Organic Chemistry,* McOmie, ed., Plenum Press, NY, N.Y. (1973); and, *Protective Groups in Organic Synthesis,* Greene, ed., John Wiley & Sons, NY, N.Y. (1981) for the teaching of protective groups which may be useful in the preparation of compounds of the present invention.

By way of example only, useful amino-protecting groups may include, for example, $C_1$–$C_{10}$ alkanoyl groups such as formyl, acetyl, dichloroacetyl, propionyl, hexanoyl, 3,3-diethylhexanoyl, γ-chlorobutryl, and the like; $C_1$–$C_{10}$ alkoxycarbonyl and $C_5$–$C_{15}$ aryloxycarbonyl groups such as tert-butoxycarbonyl, benzyloxycarbonyl, allyloxycarbonyl, 4-nitrobenzyloxycarbonyl, fluorenylmethyloxycarbonyl and cinnamoyloxycarbonyl; halo-($C_1$–$C_{10}$)-alkoxycarbonyl such as 2,2,2-trichloroethoxycarbonyl; and $C_1$–$C_{15}$ arylalkyl and alkenyl group such as benzyl, phenethyl, allyl, trityl, and the like. Other commonly used amino-protecting groups are those in the form of enamines prepared with β-keto-esters such as methyl or ethyl acetoacetate.

Useful carboxy-protecting groups may include, for example, $C_1$–$C_{10}$ alkyl groups such as methyl, tert-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri-($C_1$–$C_3$ alkyl)silyl, such as trimethylsilyl, β-p-toluenesulfonylethyl, β-p-nitrophenyl-thioethyl, 2,4,6-trimethylbenzyl, β-methylthioethyl, phthalimidomethyl, 2,4-dinitrophenylsulphenyl, 2-nitrobenzhydryl and related groups.

Similarly, useful hydroxy protecting groups may include, for example, the formyl group, the chloroacetyl group, the benzyl group, the benzhydryl group, the trityl group, the 4-nitrobenzyl group, the trimethylsilyl group, the phenacyl group, the tert-butyl group, the methoxymethyl group, the tetrahydropyranyl group, and the like.

With respect to the preferred embodiment of an oligopeptide combined with the anthracycline antibiotic doxorubicin, the following Reaction Schemes illustrate the synthsis of the conjugates of the instant invention.

REACTION SCHEME I

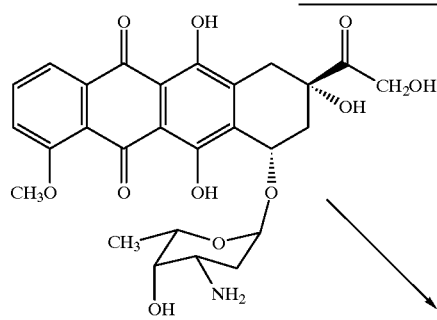

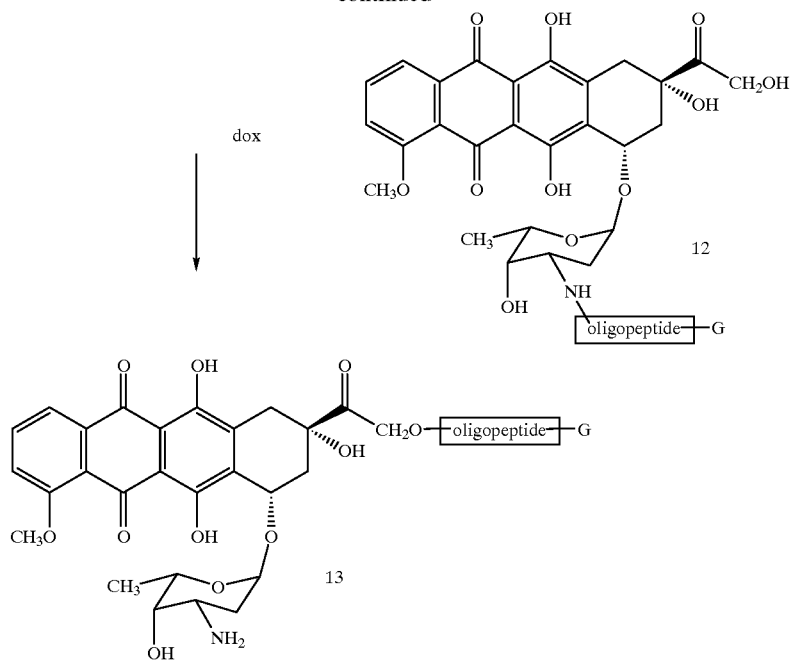
G is a hydrophilic N-terminus blocking group
REACTION SCHEME II
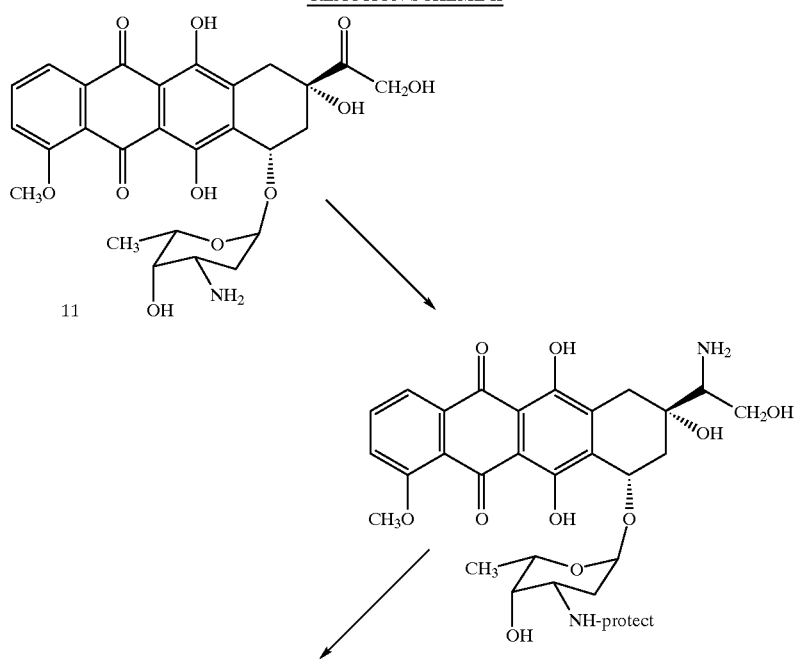

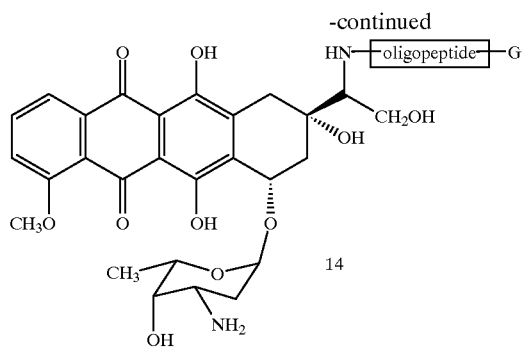
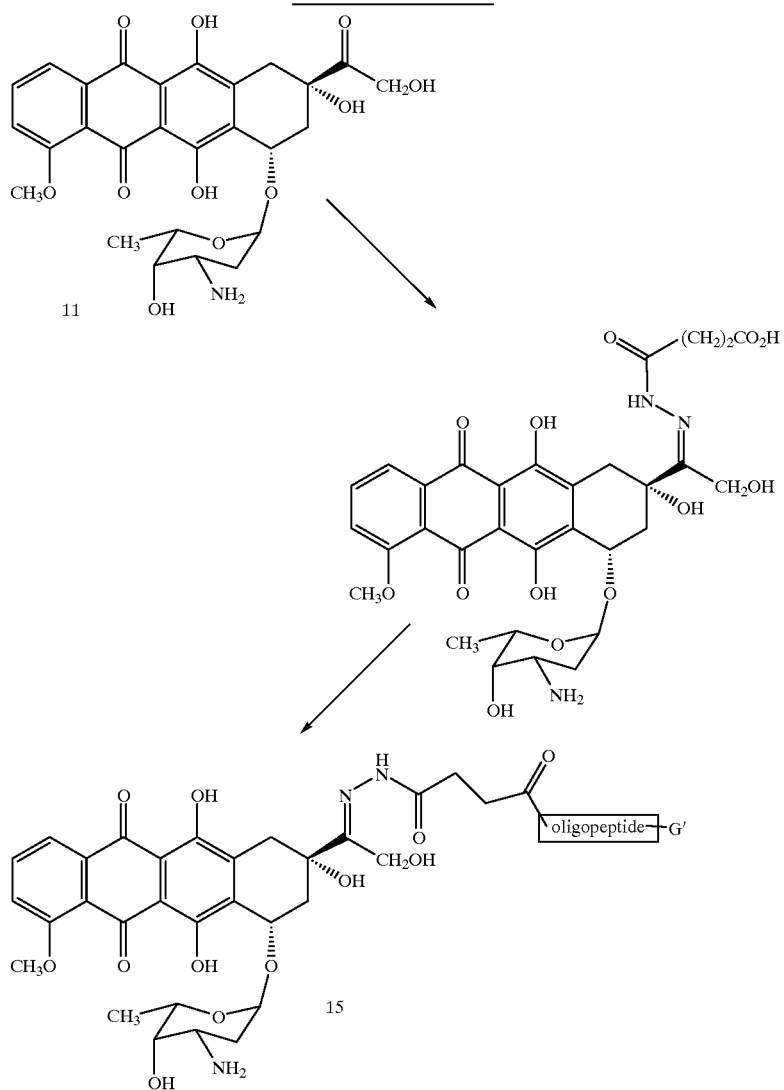
G′ is a hydrophilic C-terminal moiety

REACTION SCHEME IV

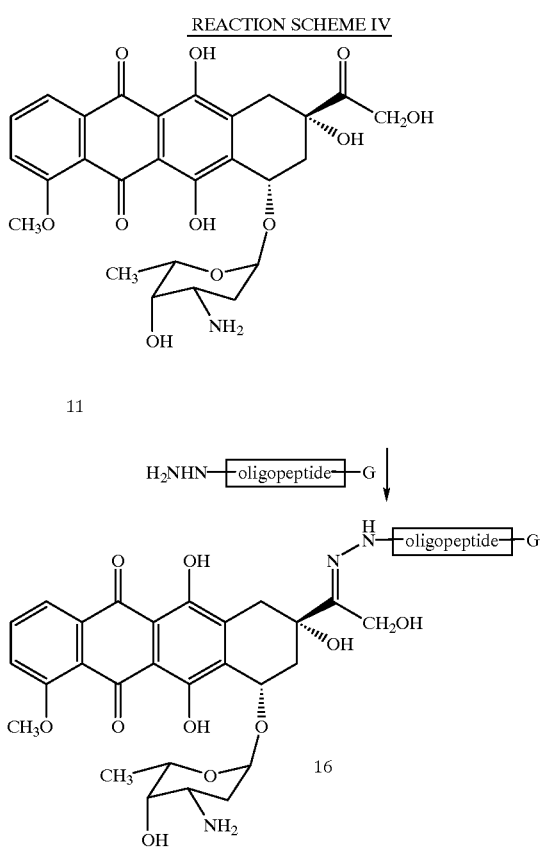

Reaction Scheme VI illustrates preparation of conjugates of the oligopeptides of the instant invention and the vinca alkaloid cytotoxic agent vinblastine wherein the attachment of vinblastine is at the C-terminus of the oligopeptide. The use of the 1,3-diaminopropane linker is illustrative only; other spacer units between the carbonyl of vinblastine and the C-terminus of the oligopeptide are also envisioned. Furthermore, Scheme VI illustrates a synthesis of conjugates wherein the C-4-position hydroxy moiety is reacetylated following the addition of the linker unit. Applicants have discovered that the desacetyl vinblastine conjugate is also efficacious and may be prepared by eliminating the steps shown in Reaction Scheme VI of protecting the primary amine of the linker and reacting the intermediate with acetic anhydride, followed by deprotection of the amine. Conjugation of the oligopeptide at other positions and functional groups of vinblastine may be readily accomplished by one of ordinary skill in the art and is also expected to provide compounds useful in the treatment of prostate cancer.

REACTION SCHEME V

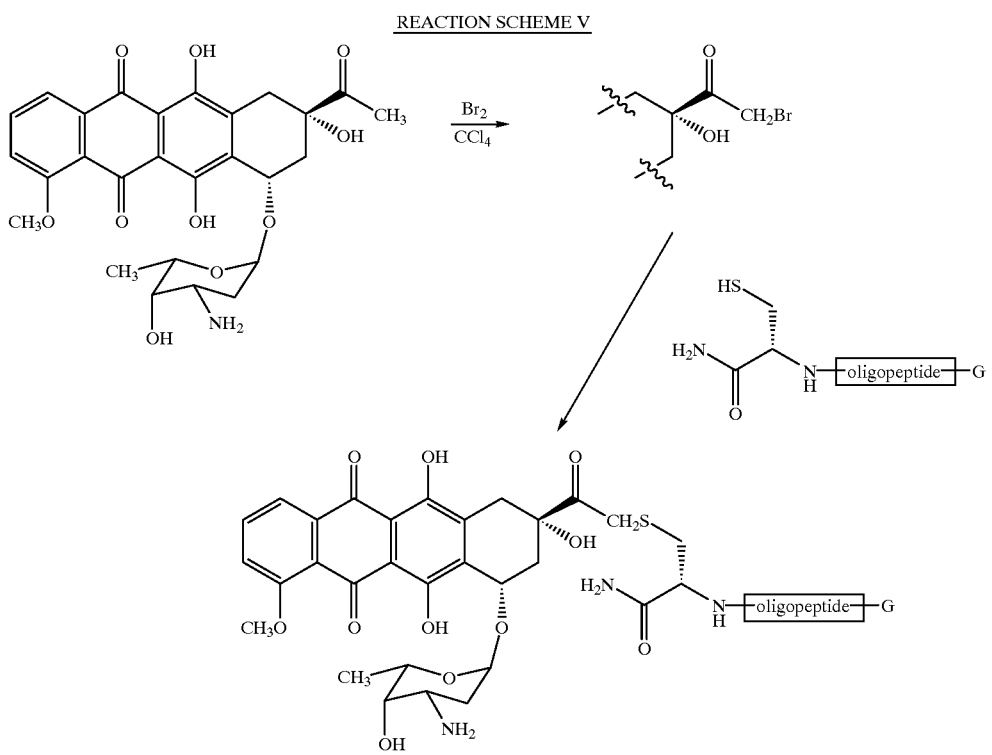

REACTION SCHEME VI

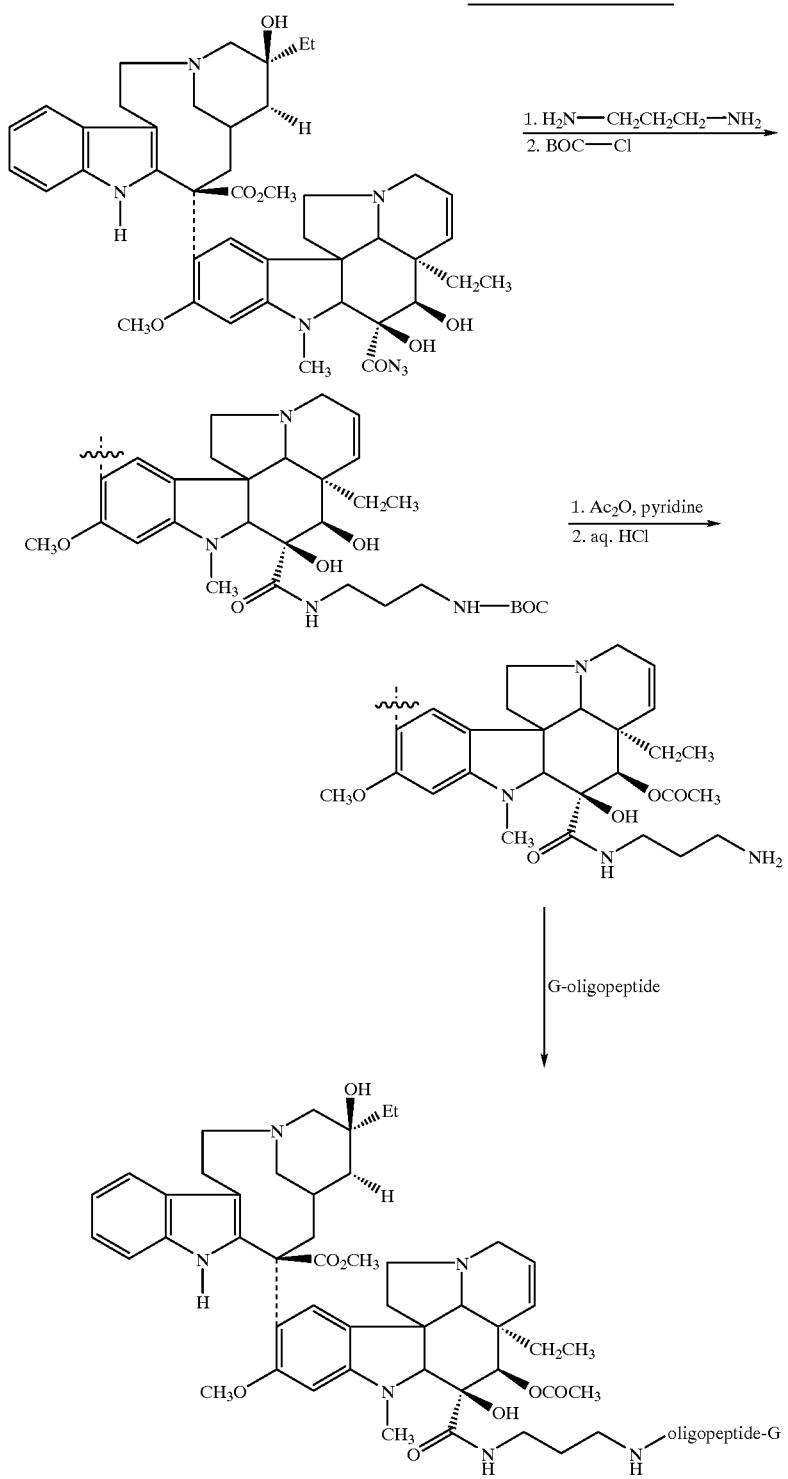

The oligopeptide-cytotoxic agent conjugates of the invention are administered to the patient in the form of a pharmaceutical composition which comprises a conjugate of of the instant invention and a pharmaceutically acceptable carrier, excipient or diluent therefor. As used, "pharmaceutically acceptable" refers to those agents which are useful in the treatment or diagnosis of a warm-blooded animal including, for example, a human, equine, procine, bovine, murine, canine, feline, or other mammal, as well as an avian or other warm-blooded animal. The preferred mode of administration is parenterally, particularly by the intravenous, intramuscular, subcutaneous, intraperitoneal, or intralymphatic route. Such formulations can be prepared using carriers, diluents or excipients familiar to one skilled in the art. In this regard, See, e.g. *Remington's Pharmaceutical Sciences,* 16th ed., 1980, Mack Publishing Company, edited by Osol et al. Such compositions may include proteins, such as serum proteins, for example, human serum albumin, buffers or buffering substances such as phosphates, other salts, or electrolytes, and the like. Suitable diluents may include, for example, sterile water, isotonic saline, dilute aqueous dextrose, a polyhydric alcohol or mixtures of such alcohols, for example, glycerin, propylene glycol, polyethylene glycol and the like. The compositions may contain preservatives such as phenethyl alcohol, methyl and propyl parabens, thimerosal, and the like. If desired, the composition can include about 0.05 to about 0.20 percent by weight of an antioxidant such as sodium metabisulfite or sodium bisulfite.

As used herein, the term "composition" is intended to encompass a product comprising the specified ingredients in the specific amounts, as well as any product which results, directly or indirectly, from combination of the specific ingredients in the specified amounts.

For intravenous administration, the composition preferably will be prepared so that the amount administered to the patient will be from about 0.01 to about 1 g of the conjugate. Preferably, the amount administered will be in the range of about 0.2 g to about 1 g of the conjugate. The conjugates of the invention are effective over a wide dosage range depending on factors such as the disease state to be treated or the biological effect to be modified, the manner in which the conjugate is administered, the age, weight and condition of the patient as well as other factors to be determined by the treating physician. Thus, the amount administered to any given patient must be determined on an individual basis.

One skilled in the art will appreciate that although specific reagents and reaction conditions are outlined in the following examples, modification can be made which are meant to be encompassed by the spirit and scope of the invention. The following preparations and examples, therefore, are provided to further illustrate the invention, and are not limiting.

EXAMPLES

Example 1

Preparation of Oligopeptides which Comprise the PSA Mediated Cleavage Site

Blocked oligopeptides were prepared by solid-phase synthesis, using a double coupling protocol for the introduction of amino acids on the Applied Biosystems model 430 A automated peptide synthesizer. Deprotection and removal of the oligopeptide from the resin support were achieved by treatment with liquid hydrofluoric acid. The oligopeptides were purified by preparative high pressure liquid chromatography on reverse phase C18 silica columns using an aqueous 0.1% trifluoroacetic acid/acetonitrile gradient. Identity and homogeneity of the oligopeptides were confirmed by amino acid composition analysis, high pressure liquid chromatography, and fast atom bombardment mass spectral analysis. The oligopeptides that were prepared by this method are shown in Table 2.

TABLE 2

| SEQ.ID.NO. | PEPTIDE/PEPTIDE-DOX CONJUGATE | Time to 50% Substrate Cleavage by York PSA (Min) |
|---|---|---|
| 103 | Ac-ANKASYQ-SL-acid | 135 |
| 104 | Ac-ANKASYQ-SL-acid | 220 |
| 105 | Ac-hR(CHA)Q-SNle-acid | 200 (PS) |
| 106 | Ac-ShRYQ-SNle-acid | 25 (PS) |
| 107 | Ac-ShRChgQ-SNle-acid | INSOLUBLE |
| 108 | Ac-hRSSYQ-SNle-acid | 25 (PS) |
| 109 | AChRSSChgQ-SL-acid | 120(45*) |
| 66 | 2-hydroxyacetyl-ShRChgQ-SL-acid | 120(30*) |
| 110 | Ac-hRSSYQ-SNle-acid | 25 (PS) |
| 64 | 2-hydroxyacetyl-hRSSYQ-SNle-acid | 45 |
| 111 | Ac-hRASChgQ-SL-acid | 50 |
| 68 | 2-hydroxyacetyl-hRASChgQ-SL-acid | 70 |
| 64 | 2-hydroxyacetyl-hRSSYQ-SL-acid | 35 (PP) |
| 67 | 2-hydroxyacetyl-hRSSChgSL-acid | (PP) |
| 69 | 2,3-dihydroxypropionylShRChgQ-SL-acid | 75 |
| 70 | 2(S)-2,3-dihydroxy propionylShRChgQSL-acid | 35* |
| 112 | 2-hydroxyacetylhRYQ-SL-acid | 105* |
| 29 | ShRChgQ-SL -acid | 4 HOUR = 8% |
| 71 | PEG(2)-S-hRChgQ-SL-acid | 30 |
| 113 | PEG(1)-ShRChgQ-SL-acid | 120* |
| 78 | 2(S)2,3-dihydroxypropionly-hRSSChgQ-SL-acid | 25* |
| 79 | PEG(2)-hRSSChgQ-SL-acid | 40* |
| 74 | PEG(2)-ShRYQ-SL-acid | 35* |
| 114 | PEG(1)-hRSSChgQ-SL-acid | 30 |
| 115 | PEG(1)-ShRYQ-SL-acid | 90 |
| 116 | PEG(15)-ShRYQ-SL-acid | 40 |
| 81 | PEG(16)-ShRYQ-SL-acid | 40 |
| 117 | PEG(17)-ShRYQ-SL-acid | 55 |
| 82 | (2R,3S)2,3,4-trihydroxybutanoyl-ShRChgQ-SL-acid | 90 |
| 83 | 2,3-dihydroxypropionyl-hRSSChgQ-SL-acid | 50 |
| 118 | PEG(2)-SSYQ-SL-acid | 150 |
| 119 | PEG(14)ShRYQ-SL-acid | 40 |
| 120 | PEG(18)ShRYQ-SL-acid | 40 |
| 121 | PEG(19)ShRYQ-SL-acid | 60 |
| 94 | (d)2,3-dihydroxypropionyl-3PAL-SSChgQSL-acid | 80 |
| 63 | PEG(2)SSSChgQ-SL-acid | 150 |
| 101 | PEG(2)-3PAL-SSChgQ-SL-acid | 80 |
| 87 | (I)2,3-dihydroxypropionyl-SSSChgQ-SL-acid | 80 |

TABLE 2-continued

| SEQ.ID.NO. | PEPTIDE/PEPTIDE-DOX CONJUGATE | Time to 50% Substrate Cleavage by York PSA (Min) |
|---|---|---|
| 61 | (OH-Ac)SSSChgQ-SL-acid | 120 |
| 122 | (I)2,3-dihydroxypropionyl-SSChgQ-SL-acid | 180 |
| 87 | (I)2,3-dihydroxypropionyl-SSSChgQ-SL-acid | 110 |
| 123 | (I)2,3-dihydroxypropionyl-3PAL-SSChgQ-SL-acid | 70 |
| 124 | 2,3-dihydroxypropionyl-SSSChgQ-SL-acid | 120 |
| 125 | 2,3-dihydroxypropionyl-ShRYQ-SL-acid | 35 |
| 62 | 2-hydroxyacetyl-SSChgQ-SL-acid | 180 |
| 125 | 2,3-dihydroxypropionyl-ShRYQ-SL-acid | 50 |
| 101 | PEG(4)-β-PAL-SSChgQ-SL-acid | 60 |
| 126 | Ac-SSSChgQ-SV-acid | |
| 127 | Ac-PSSChgQ-SV-acid | |
| 128 | 2,3-dihydroxypropionyl-GSSChgQ-SL-acid | 160 |
| 96 | 2,3-dihydroxypropionyl-hSSSChgQ-SL-acid | 160 |

Example 2
Assessment of the Recognition of Oligopeptides by Free PSA

The oligopeptides prepared as described in Example 1 were individually dissolved in PSA digestion buffer (12 mM tris(hydroxymethyl)-aminomethane pH8.0, 25 mM NaCl, 0.5 mM $CaCl_2$) and the solution added to PSA at a molar ration of 100 to 1. The reaction is quenched after various reaction times by the addition of trifluoroacetic acid (TFA) to a final 1% (volume/volume). The quenched reaction was analyzed by HPLC on a reversed-phase C18 column using an aqueous 0.1% TFA/acetonitrile gradient. The results of the assessment are shown in Table 2. Table 2 shows the amount of time (in minutes) required for 50% cleavage of the noted oligopeptides with enzymatically active free PSA. Oligopeptides containing free amine moieties (ie. comprising hArg, Orn, Lys and or 3PAL) were tested as TFA salts. All other oligopeptides were tested as neutral compounds.

Example 3
Preparation of N-(2-Hydroxyacetyl)-Ser-Ser-Ser-Chg-Gln-Ser-Leu-Dox (3-3)

Step A: 2-HO-Ac-Ser(Bzl)-Ser(Bzl)-Ser(Bzl)-Chg-Gln-Ser-Leu-PAM Resin (3-1)

Starting with 0.5 mmol (0.67 g) Boc-Leu-PAM resin (Applied Biosystems Inc.—ABI), the protected peptide was synthesized on a 430 A ABI peptide synthesizer. The protocol used a 4 fold excess (2 mmol) of each of the following protected amino acids: Boc-Ser(OBzl), Boc-Gln, Boc-Chg. Coupling was achieved using DCC and HOBT activation in methyl-2-pyrrolidinone. Removal of the Boc group was performed using 50% TFA in methylene chloride and the TFA salt neutralized with diisopropylethylamine. 2-Hydroxyacetic acid was used for the introduction of the N terminal blocking group, which was also carried out on the peptide synthesizer. At the completion of the synthesis, the peptide resin was dried to provide the title resin-peptide conjugate.

Step B: 2-HO-Ac-Ser-Ser-Ser-Chg-Ser-Leu-OH (3-2)

The protected peptide resin (3-1), 1.2 g, was treated with HF (15 ml) for 1 hr at 0° C. in the presence of anisole (1.5 ml). After evaporation of the HF, the residue was washed with ether 3 times, and extracted with 20% HOAc. The crude peptide products from the HF-cleavage after lyophilization were purified by preparatory HPLC on a Delta-Pak C18 column with 0.1% trifluoroacetic acid-aqueous acetonitrile solvent systems using 100–70% 0.1% TFA-$H_2O$, 60 min linear gradient. Fractions containing product of at least 99% (HPLC) purity were combined to provide the title blocked peptide.

FABMS: 804.85

Peptide Content: 1.03NMOle/mg.

HPLC: 99% pure @214, retention times=11.16 min, (Vydac $C_{18}$, gradient of 95% A/B to 50% A/B over 30 min, A=0.1% TFA-$H_2O$, B=0.1% TFA-$CH_3CN$)

Step C: 2-HO-Ac-Ser-Ser-Ser-Chg-Ser-Leu-Dox (3-3)

A solution of 241 mg (0.30 mmol) of OH-Ac-Ser-Ser-Ser-Chg-Gln-Leu-OH (3-2) in 3.0 ml anhyd. N-methyl pyrrolidine (NMP) (or DMF), 46 mg (0.30 mmol) of HOBT, 63 mg (0.33 mmol) of EDC, 46 mg (0.09 mmol) of doxorubicin was added and pH was adjusted with diisopropylethylamine (DIEA) to pH 8.5. The solution was stirred at 0° C. for 11 hrs., and then reaction was quenched by $H^+$. The organic solvent was removed under reduced pressure and the residue was diluted with 15 ml of water, and purified by preparative HPLC using a $NH_4Ac$ (4 g/4 L)-$CH_3CN$ gradient, ie. 95–50% A, 60 min. Lyophilization of pure fractions gave a red powder. The red powder was dissolved in distil. $H_2O$, filtered, and lyophilized to provide the title conjugate (1-3).

$ES^+ + NH_4^+$: 1347.61

Peptide Content: 541.72 NMOle/mg.

HPLC: 99% pure @214, retention times=20.8 min, (Vydac $C_{18}$, gradient of 95% A/B to 50% A/B over 30 min, A=0.1% TFA-$H_2O$, B=0.1% TFA, $CH_3CN$)

Example 4
Preparation of N-[2-{2-(2-methoxyethoxy)ethoxy}acetyl]-Ser-Ser-Ser-Chg-Gln-Ser-Leu-Dox The title conjugate was prepared in the manner described in Example 3, but substituting 2-{2-(2-methoxyethoxy)ethoxy}acetic acid for 2-hydroxyacetic acid in Step A.

$ES^+ + NH_4+$: 1450.72

Peptide Content: 534.36 NMOle/mg.

HPLC: 99% pure @214, retention times=21.99 min, (Vydac $C_{18}$, gradient of 95% A/B to 50% A/B over 30 min, A=0.1% TFA-$H_2O$, B=0.1% TFA, $CH_3CN$)

Example 5
Preparation of N-2(R)-2,3-dihydroxypropionyl-Ser-Ser-Ser-Chg-Gln-Ser-Leu-Dox (5-3)

Step A: N-2(R)-2,3-dihydroxypropionyl-Ser(Bzl)-Ser(Bzl)-Ser(Bzl)-Chg-Gln-Ser-Leu-PAM Resin (5-1)

Starting with 0.5 mmol (0.67 g) Boc-Leu-PAM resin, the protected peptide was synthesized on a 430 A ABI peptide synthesizer. The protocol used a 4 fold excess (2 mmol) of each of the following protected amino acids: Boc-Ser (OBzl), Boc-Gln and Boc-Chg. Coupling was achieved using DCC and HOBT activation in methyl-2-pyrrolidinone. Removal of the Boc group was performed using 50% TFA in methylene chloride and the TFA salt neutralized with diisopropylethylamine. D-Glyceric acid, which was converted from D-Glyceric acid calcium salt, was used for the introduction of the N terminal blocking group. At the completion of the synthesis, the peptide resin was dried to provide the title resin-peptide conjugate.

HPLC: 99% pure @214, retention times=20.57 min, (Vydac $C_{18}$, gradient of 95% A/B to 50% A/B over 30 min, A=0.1% TFA-$H_2O$, B=0.1% TFA, $CH_3CN$)

Table 3 shows other blocked peptide-doxorubicin conjugates that were prepared by the procedures described in Examples 3–6, but utilizing the appropriate amino acid residues and blocking group acylation.

TABLE 3

| SEQ. ID.NO. | PEPTIDE/PEPTIDE-DOX CONJUGATE | Time to 50% Substrate Cleavage by York PSA (Min) |
|---|---|---|
| 64 | 2-hydroxyacetyl-HomoRSSYQ-SNle-DOX(3') | 60* |
| 66 | 2-hydroxyacetyl-SHomoRChgQ-SL-DOX(3') | 15 |
| 67 | 2-hydroxyacetyl-HomoRSSChgQ-SL-DOX(3') | 12 |
| 68 | 2-hydroxyacetyl-HomoRASChgQ-SL-DOX(3') | 10 |
| 69 | (d)2,3-dihydroxypropionyl-SHomoRChgQ-SL-DOX(3') | 65 |
| 70 | (l)2,3-dihydroxypropionyl-SHomoRChgQ-SL-DOX(3') | 15 |
| 71 | PEG(2)-SHomoRChgQ-SL-DOX(3') | 25 |
| 72 | PEG(2)-HomoRchgQ-SL-DOX(3') | 4 HOUR = 12% |
| 73 | (2R,3S)2,3,4-trihydroxybutanoyl-HomoRChgQ-SL-DOX(3') | 4 HOUR = 0% |
| 74 | PEG(2)-SHomoRYQ-SL-DOX(3') | 35 |
| 75 | PEG(2)-HomoRYQ-SSSL-DOX(3') | 4 HQUR = 40% (PS) |
| 76 | PEG(2)-KY9-SSSL-DOX(3') | 4 HOUR = 20% (PS) |
| 77 | 2-hydroxyacetyl-HomoRSSYQ-SL-DOX(3') | 16 (PS) |
| 78 | (l)2,3-dihydroxypropionylHomoRSSChgQSL-DOX(3') | 12 |
| 79 | PEG(2)-HomoRSSChgQ-SL-DOX(3') | 11 |
| 80 | 2-hydroxyacetyl-SYQ-SSSL-DOX(3') | (PS) |
| 81 | PEG(16)-SHomoRYQ-SL-DOX(3') | 65 |
| 82 | (2R,3S)2,3,4-trihydroxybutanoyl-SHomoRChgQ-SL-DOX(3') | 45 |
| 83 | PEG(2)-SHomoRYQ-SL-DOX(3') | 60 |
| 84 | (d)2,3-dihydroxypropionyl-HomoRSSChgQSL-DOX(3') | 12 |
| 85 | (l)2,3-dihydroxypropionylSSSChgQ-S(dL)-DOX(3') | 180 |
| 86 | (d)2,3-dihydroxypropionylSSSChgQ-SL-DOX(3') | 55 |
| 87 | (l)2,3-dihydroxypropionylSSSChgQ-SL-DQX (3') | 25 |
| 88 | (l)2,3-dihydroxypropionylSSChgQ-S(dL)-DOX(3') | 3 HOUR = 22% |
| 89 | (d)2,3-dihydroxypropionylSSChgQ-SL-DOX(3') | 120 |
| 91 | PEG(2)SSChgQ-SL-DOX(3') | 90 |
| 92 | PEG(2)-SSSChgQ-S(dL)-DOX(3') | 3 HOURS = 46% |
| 63 | PEG(2)-SSSChgQ-SL-DOX(3') | 60 |
| 94 | (d)2,3-dihydroxypropionyl-3PALSSChgQ-SL-DOX(3'):AcOH | 12 (PS) |
| 95 | (l)2,3-dihydroxypropionyl-SSChgQ-SL-DOX(3') | 25 |
| 61 | 2-hydroxyacetyl-SSSChgQ-SL-DOX(3') | 25 |
| 96 | 2,3-dihydroxypropionyl-HomoSSSChgQ-SL-DOX(3') | 35 |
| 97 | PEG(2)-ASChgQ-SL-DOX(3') | 45 |
| 98 | PEG(6)-ASChgQ-SL-DOX(3') | 160 |
| 62 | 2-hydroxyacetyl-SSChgQ-SL-DOX(3') | 45 |

Step B: N-2(R)-2,3-dihydroxypropionyl-Ser-Ser-Ser-Chg-Gln-Ser-Leu-Dox (5-3)

The title conjugate was prepared in the manner described in Example 3, Steps B and C, but substituting the resin peptide conjugate 5-1 for the resin-peptide conjugate used in Example 3, Step B.

$ES^+ + NH_4^+$: 1377.55

Peptide Content: 620.85 NMOle/mg.

HPLC: 99% pure @214, retention times=20.71 min, (Vydac $C_{18}$, gradient of 95% A/B to 50% A/B over 30 min, A=0.1% TFA-$H_2O$, B=0.1% TFA, $CH_3CN$)

Example 6

Preparation of N-2(S)-2,3-dihydroxypropionyl-Ser-Ser-Ser-Chg-Gln-Ser-Leu-Dox

The title conjugate was prepared in the manner described in Example 5, but substituting L-glyceric acid for D-glyceric acid in Step A.

$ES^+ + NH_4^+$: 1377.62

Peptide Content: 641.59 NMOle/mg.

Example 7

Assessment of the Recognition of Oligopeptide-Doxorubicin Conjugates by Free PSA The conjugates prepared as described in Examples 3–6 were individually dissolved in PSA digestion buffer (50 mM tris(hydroxymethyl)-aminomethane pH7.4, 140 mM NaCl) and the solution added to PSA at a molar ration of 100 to 1. The reaction is quenched after various reaction times by the addition of trifluoroacetic acid (TFA) to a final 1% (volume/volume). The quenched reaction was analyzed by HPLC on a reversed-phase C18 column using an aqueous 0.1% TFA/acetonitrile gradient. The results of the assessment are shown in Table 3. Table 3 shows the amount of time (in minutes) required for 50% cleavage of the noted oligopeptide-cytotoxic agent conjugates with enzymatically active free PSA. If no salt is indicated for the conjugate, the free conjugate was tested. An alternative PSA digestion buffer (12 mM tris(hydroxymethyl )-aminomethane pH8.0, 25 mM NaCl, 0.5 mM $CaCl_2$) was utilized in t he assessment of the 2-hydroxyacetyl-hArgSerSerTyrGln-Ser-Nle-DOX (3') (SEQ.ID.NO.: 30) conjugate.

Example 8
In vitro Assay of Cytotoxicity of Peptidyl Derivatives of Doxorubicin The cytotoxicities of the cleaveable oligopeptide-doxorubicin conjugates, prepared as described in Examples 3–6, against a line of cells which is known to be killed by unmodified doxorubicin was assessed with an Alamar Blue assay. Specifically, cell cultures of LNCap prostate tumor cells or DuPRO cells in 96 well plates was diluted with medium containing various concentrations of a given conjugate (final plate well volume of 200 µl). The cells were incubated for 3 days at 37° C., 20 µl of Alamar Blue is added to the assay well. The cells were further incubated and the assay plates were read on a EL-310 ELISA reader at the dual wavelengths of 570 and 600 nm at 4 and 7 hours after addition of Alamar Blue. Relative percentage viability at the various concentration of conjugate tested was then calculated versus control (no conjugate) cultures. Results of this assay are shown in Table 4. If no salt is indicated, the free conjugate was tested.

Harlan Sprague Dawley male nude mice (10–12 weeks old) are restrained without anesthesia and are inoculated with 0.5 mL of cell suspension on the left flank by subcutaneous injection using a 22 G needle. Mice are either given approximately $5 \times 10^5$ DuPRO cells or $1.5 \times 10^7$ LNCaP.FGC cells.

Following inoculation with the tumor cells the mice are treated under one of two protocols:

Protocol A

One day after cell inoculation the animals are dosed with a 0.1–0.5 mL volume of test conjugate, doxorubicin or vehicle control (sterile water). Dosages of the conjugate and doxorubicin are initially the maximum non-lethal amount, but may be subsequently titrated lower. Identical doses are administered at 24 hour intervals for 5 days. After 10 days, blood samples are removed from the mice and the serum level of PSA is determined. Similar serum PSA levels are determined at 5–10 day intervals. At the end of 5.5 weeks the mice are sacrificed and weights of any tumors present are measured and serum PSA again determined. The animals' weights are determined at the beginning and end of the assay.

TABLE 4

| SEQ. ID.NO. | PEPTIDE/PEPTIDE-DOX CONJUGATE | LNCaP Cell Kill in 72 HRS, {48 HRS} EC 50 (µM) |
|---|---|---|
| 64 | 2-hydroxyacetyl-hRSSYQ-SNle-DOX(3') | 3.6 (DUPRO > 100) |
| 66 | 2-hydroxyacetyl-ShRChgQ-SL-DOX(3') | 5.1 (DUPRO > 100) |
| 67 | 2-hydroxyacetyl-hRSSChgQ-SL-DOX(3') | 5.5 (DUPRO > 100) |
| 68 | 2-hydroxyacetyl-hRASChgQ-SL-DOX(3') | 7.9 (DUPRO > 100) (PS) |
| 69 | (d)2,3-dihydroxypropionyl-ShRChgQ-SL-DOX(3') | 5.8 (DUPRO > 100) n = 2 |
| 71 | PEG(2)-ShRChgQ-SL-DOX(3') | 8.1 (DuPRO > 100) |
| 72 | PEG(2)-hRChgQ-SL-DOX(3') | INSOLUBLE |
| 73 | (2R,3S) 2,3,4-trihydroxybutanoyl-hRChgQ-SL-DOX(3') | PS |
| 74 | PEG(2)-ShRYQ-SL-DOX(3') | 4.5 (DuPRO > 100) |
| 75 | PEG(2)-hRYQ-SSSL-DOX(3') | 14 (DuPRO > 100) (PS) |
| 76 | PEG(2)-KYQ-SSSL-DOX(3') | 12.8 (DUPRO > 100) (PS) |
| 77 | 2-hydroxyacetyl-hRSSYQ-SL-DOX(3') | 13.6 (DUPRO > 100) (PS) |
| 78 | (I)2,3-dihydroxypropionylhRSSChgQSL-DOX(3') | 7.5 (DuPRO > 100) |
| 79 | PEG(2)-hRSSChgQ-SL-DOX(3') | 5.7 (DuPRO > 100) |
| 80 | 2-hydroxyacetyl-SYQ-SSSL-DOX(3') | 18.8 (DuPRO = 50) (PS) |
| 81 | PEG(16)-ShRYQ-SL-DOX(3') | 45 (DuPRO = 100) |
| 82 | (2R,3S) 2,3,4-trihydroxybutanoyi-ShRChgQ-SL-DOX(3') | 14.1 (DuPRO > 100) |
| 83 | PEG(2)-ShRYQ-SL-DOX(3') | 34 (DUPRO = 100) n = 2 |
| 84 | (d)2,3-dihydroxypropionyl-hRSSChgQSL-DOX(3') | 7.7 (DuPRO > 100) n = 2 |
| 85 | (I)2,3-dihydroxypropionylSSSChgQ-S(dL)-DQX (3') | 91 (DuPRO > 100) |
| 86 | (d)2,3-dihydroxypropionylSSSChgQ-SL-DOX(3') | 5.8 (DUPRO > 100) n = 3 |
| 87 | (I)2,3-dihydroxypropionylSSSChgQ-SL-DOX(3') | 5.5 (DuPRO > 100) |
| 88 | (I)2,3-dihydroxypropionylSSSChgQ-S(dL)-DOX(3') | > 100 (DuPRO > 100) |
| 89 | (d)2,3-dihydroxypropionylSSSChgQ-SL-DOX(3') | 9.1 (DUPRO > 100) |
| 91 | PEG(2)SSChgQ-SL-DOX(3') | 8.8 (DUPRO > 100) |
| 63 | PEG(2)-SSSChgQ-SL-DOX(3') | 10 (DuPRO > 100) n = 2 |
| 94 | (d)2,3-dihydroxypropionyl-3PAL-SSChgQ-SL-DOX(3'). AcOH | 5.5 (DuPRO > 100) |
| 95 | (I)2,3-dihydroxypropionyl-SSChgQ-SL-DOX(3') | 13 (DuPRO > 100) n = 2 |
| 61 | 2-hydroxyacetyl-SSSChgQ-SL-DOX(3') | 7.2 (DuPRO > 100) n = 3 |
| 96 | 2,3-dihydroxypropionyl-hSSSChgQ-SL-DOX(3') | 5.1 (DuPRO = 90) |
| 97 | PEG(2)-ASChgQ-SL-DOX(3') | 5.6 (DuPRO 100) n = 2 |
| 98 | PEG(6)-ASChgQ-SL-DOX(3') | 12 (DuPRO = 100) |
| 62 | 2-hydroxyacetyl-SSChgQ-SL-DOX(3') | 4.8 (DuPRO > 100) |

Example 9
In vivo Efficacy of Peptidyl-Cytotoxic Agent Conjugates

LNCaP.FGC or DuPRO-1 cells are trypsinized, resuspended in the growth medium and centifuged for 6 mins. at 200×g. The cells are resuspended in serum-free α-MEM and counted. The appropriate volume of this solution containing the desired number of cells is then transferred to a conical centrifuge tube, centrifuged as before and resuspended in the appropriate volume of a cold 1:1 mixture of α-MEM-Matrigel. The suspension is kept on ice until the animals are inoculated.

Protocol B

Ten days after cell inoculation, blood samples are removed from the animals and serum levels of PSA are determined. Animals are then grouped according to their PSA serum levels. At 14–15 days after cell inoculation, the animals are dosed with a 0.1–0.5 mL volume of test conjugate, doxorubicin or vehicle control (sterile water). Dosages of the conjugate and doxorubicin are initially the maximum non-lethal amount, but may be subsequently titrated lower. Identical doses are administered at 24 hour intervals for 5 days. Serum PSA levels are determined at 5–10 day intervals. At the end of 5.5 weeks the mice are sacrificed, weights of any tumors present are measured and serum PSA again determined. The animals' weights are determined at the beginning and end of the assay.

Example 10

In vitro Determination of Proteolytic Cleavage of Conjugates by Endogenous Non-PSA Proteases Step A: Preparation of Proteolytic Tissue Extracts All procedures are carried out at 4° C. Appropriate animals are sacrificed and the relevant tissues are isolated and stored in liquid nitrogen. The frozen tissue is pulverized using a mortar and pestle and the pulverized tissue is transferred to a Potter-Elvejeh homogenizer and 2 volumes of Buffer A (50 mM Tris containing 1.15% KCl, pH 7.5) are added. The tissue is then disrupted with 20 strokes using first a lose fitting and then a tight fitting pestle. The homogenate is centrifuged at 10,000×g in a swinging bucket rotor (HB4-5), the pellet is discarded and the re-supernatant centrifuged at 100,000×g (Ti 70). The supernatant (cytosol) is saved.

The pellet is resuspended in Buffer B (10 mM EDTA containing 1.15% KCl, pH 7.5) using the same volume used in step as used above with Buffer A. The suspension is homogenized in a dounce homogenizer and the solution centrifuged at 100,000×g. The supernatant is discarded and the pellet resuspended in Buffer C (10 mM potassium phosphate buffer containing 0.25 M sucrose, pH 7.4), using ½ the volume used above, and homogenized with a dounce homogenizer.

Protein content of the two solutions (cytosol and membrane) is determine using the Bradford assay. Assay aliquots are then removed and frozen in liquid $N_2$. The aliquots are stored at −70° C.

Step B: Proteolytic Cleavage Assay

For each time point, 20 microgram of peptide-doxorubicin conjugate and 150 micrograms of tissue protein, prepared as described in Step A and as determined by Bradford in reaction buffer are placed in solution of final volume of 200 microliters in buffer (50 mM TRIS, 140 mM NaCl, pH 7.2). Assay reactions are run for 0, 30, 60, 120, and 180 minutes and are then quenched with 9 microliters of 0.1 M $ZnCl_2$ and immediately placed in boiling water for 90 seconds. Reaction products are analyzed by HPLC using a VYDAC C18 15 cm column in water/acetonitrile (5% to 50% acetonitrile over 30 minutes).

What is claimed is:
1. A conjugate which is selected from:

[Structure of doxorubicin with X substituent on the amino sugar]

wherein X is:

(SEQ.ID.NO.: 61)

HO-CH2-C(O)-SerSerSerChgGlnSerLeu-, (SEQ.ID.NO.: 62)

HO-CH2-C(O)-SerSerChgGlnSerLeu-, (SEQ.ID.NO.: 63)

H3C-O-CH2CH2-O-CH2CH2-O-CH2-C(O)-SerSerSerChgGlnSerLeu-, or an optical isomer or pharmaceutically acceptable salt thereof.

2. A conjugate which is selected from:
2-hydroxyacetyl-hArgSerSerTyrGln-SerNle-DOX (3') (SEQ.ID.NO.: 64)
2-hydroxyacetyl-hArgSerSerChgGln-SerNle-DOX (3') (SEQ.ID.NO.: 65)
2-hydroxyacetyl-SerhArgChgGln-SerLeu-DOX (3') (SEQ.ID.NO.: 66)
2-hydroxyacetyl-hArgSerSerChgGln-SerLeu-DOX (3') (SEQ.ID.NO.: 67)
2-hydroxyacetyl-hArgAlaSerChgGln-SerLeu-DOX (3') (SEQ.ID.NO.: 68)
(d) 2,3-dihydroxypropionyl-SerhArgChgGln-SerLeu-DOX (3') (SEQ.ID.NO.: 69)
(l) 2,3-dihydroxypropionyl-SerhArgChgGln-SerLeu-DOX (3') (SEQ.ID.NO.: 70)
PEG(2)-SerhArgChgGln-SerLeu-DOX (3') (SEQ.ID.NO.: 71)
PEG(2)-hArgChgGln-SerLeu-DOX (3') (SEQ.ID.NO.: 72)
(2R,3S) 2,3,4-trihydroxybutanoyl-hArgChgGln-SerLeu-DOX (3') (SEQ.ID.NO.: 73)
PEG(2)-SerhArgTyrGln-SerLeu-DOX(3') (SEQ.ID.NO.: 74)
PEG(2)-hArgTyrGln-SerSerSerLeu-DOX (3') (SEQ.ID.NO.: 75)
PEG(2)-LysTyrGln-SerSerSerLeu-DOX (3') (SEQ.ID.NO.: 76)
2-hydroxyacetyl-hArgSerSerTyrGln-SerLeu-DOX (3') (SEQ.ID.NO.: 77)
(l)(2,3-dihydroxypropionyl)hArgSerSerChgGlnSerLeu-DOX (3') (SEQ.ID.NO.: 78)
PEG(2)-hArgSerSerChgGln-SerLeu-DOX (3') (SEQ.ID.NO.: 79)
2-hydroxyacetyl-SerTyrGln-SerSerSerLeu-DOX (3') (SEQ.ID.NO.: 80)
PEG(16)-SerhArgTyrGln-SerLeu-DOX (3') (SEQ.ID.NO.: 81)
(2R,3S) 2,3,4-trihydroxybutanoyl-SerhArgChgGln-SerLeu-DOX (3') (SEQ.ID.NO.: 82)
PEG(2)-SerhArgTyrGln-SerLeu-DOX (3') (SEQ.ID.NO.: 83)
(d)(2,3-dihydroxypropionyl)-hArgSerSerChgGln-SerLeu-DOX(3') (SEQ.ID.NO.: 84)
(l)(2,3-dihydroxypropionyl)SerSerSerChgGln-Ser(dLeu)-DOX (3') (SEQ.ID.NO.: 85)
(d)(2,3-dihydroxypropionyl)SerSerSerChgGln-SerLeu-DOX (3') (SEQ.ID.NO.: 86)
(l)(2,3-dihydroxypropionyl)SerSerSerChgGln-SerLeu-DOX (3') (SEQ.ID.NO.: 87)
(l)(2,3-dihydroxypropionyl)SerSerChgGln-Ser(dLeu)-DOX (3') (SEQ.ID.NO.: 88)
(d)(2,3-dihydroxypropionyl)SerSerChgGln-SerLeu-DOX (3') (SEQ.ID.NO.: 89)
PEG(2)SerSerChgGln-SerLeu-DOX (3') (SEQ.ID.NO.: 91)
(d)(2,3-dihydroxypropionyl)-3PAL-SerSerChgGln-SerLeu-DOX (3') (SEQ.ID.NO.: 94)
(l)(2,3-dihydroxypropionyl)-SerSerChgGln-SerLeu-DOX (3') (SEQ.ID.NO.: 95)
(2,3-dihydroxypropionyl)-hSerSerSerChgGln-SerLeu-DOX (3') (SEQ.ID.NO.: 96)
PEG(2)-AlaSerChgGln-SerLeu-DOX (3') (SEQ.ID.NO.: 97)
PEG(6)-SerSerChgGln-SerLeu-DOX (3') (SEQ.ID.NO.: 98)
PEG(6)-SerSerSerChgGln-SerLeu-DOX (3') (SEQ.ID.NO.: 99)
PEG(6)-AlaSerChgGln-SerLeu-DOX (3') (SEQ.ID.NO.: 100)
PEG(4)-3PALSerSerChgGln-SerLeu-DOX (3') (SEQ.ID.NO.: 101)

or an optical isomer or pharmaceutically acceptable salt thereof.

3. A conjugate which is:

(SEQ.ID.NO.: 61)

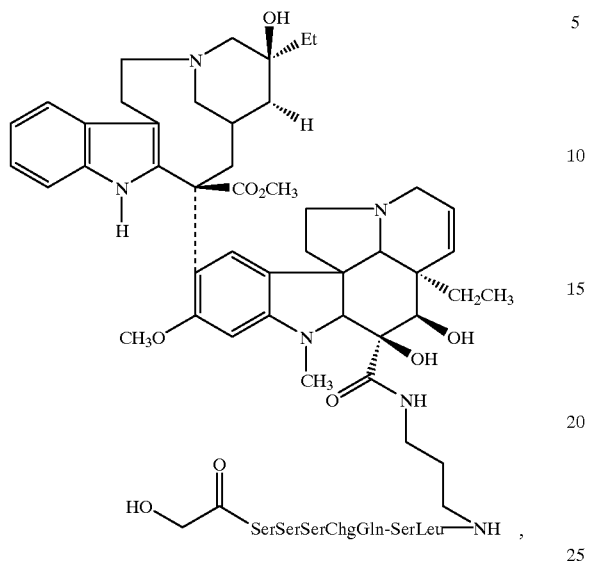

or a pharmaceutically acceptable salt or optical isomer thereof.

4. A conjugate which is:

(SEQ.ID.NO.: 102)

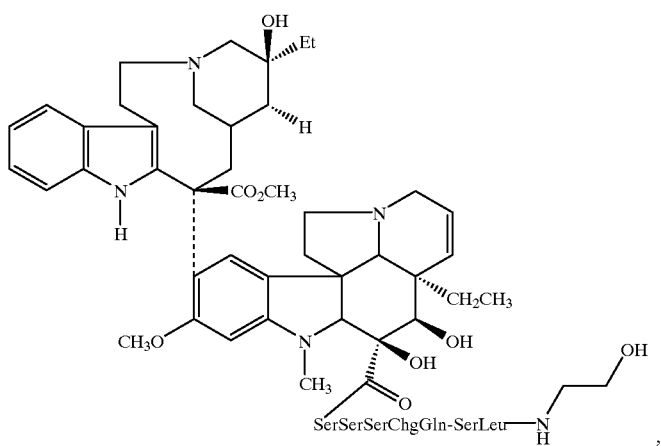

or a pharmaceutically acceptable salt or optical isomer thereof.

5. A pharmaceutical composition comprising a pharmaceutical carrier, and dispersed therein, a therapeutically effective amount of a compound of claim 1.

6. A pharmaceutical composition comprising a pharmaceutical carrier, and dispersed therein, a therapeutically effective amount of a compound of claim 2.

7. A method for treating prostate cancer which comprises administering to a mammal in need thereof a therapeutically effective amount of a composition of claim 5.

8. A method for treating prostate cancer which comprises administering to a mammal in need thereof a therapeutically effective amount of a composition of claim 6.

9. A method for treating benign prostatic hyperplasia which comprises administering to a mammal in need thereof a therapeutically effective amount of a composition of claim 5.

10. A method for treating benign prostatic hyperplasia which comprises administering to a mammal in need thereof a therapeutically effective amount of a composition of claim 6.

* * * * *